(12) United States Patent
Aston et al.

(10) Patent No.: US 12,213,957 B2
(45) Date of Patent: Feb. 4, 2025

(54) USE OF AMINOACETONITRILE COMPOUNDS FOR THE TREATMENT OF INFECTION AND DISEASE

(71) Applicant: PITNEY PHARMACEUTICALS PTY LIMITED, Claremont (AU)

(72) Inventors: Roger Aston, Claremont (AU); Richard Mollard, Claremont (AU)

(73) Assignee: PITNEY PHARMACEUTICALS PTY LIMITED, Claremont (AU)

( * ) Notice: Subject to any disclaimer, the term of this patent is extended or adjusted under 35 U.S.C. 154(b) by 0 days.

(21) Appl. No.: 17/924,537

(22) PCT Filed: May 11, 2021

(86) PCT No.: PCT/AU2021/050435
§ 371 (c)(1),
(2) Date: Nov. 10, 2022

(87) PCT Pub. No.: WO2021/226662
PCT Pub. Date: Nov. 18, 2021

(65) Prior Publication Data
US 2023/0181516 A1 Jun. 15, 2023

(30) Foreign Application Priority Data

May 11, 2020 (AU) ................................ 2020901514
May 29, 2020 (AU) ................................ 2020901776

(51) Int. Cl.
*A61K 31/277* (2006.01)
*A61P 31/14* (2006.01)
*A61P 35/00* (2006.01)

(52) U.S. Cl.
CPC ............ *A61K 31/277* (2013.01); *A61P 31/14* (2018.01); *A61P 35/00* (2018.01)

(58) Field of Classification Search
CPC .......... A61K 31/277; A61P 31/14; A61P 35/00
See application file for complete search history.

(56) References Cited

FOREIGN PATENT DOCUMENTS

| WO | 2013/138863 A1 | 9/2013 | |
|----|----|----|----|
| WO | 2014/022879 A1 | 2/2014 | |
| WO | WO 2014/022879 * | 2/2014 | ........... C07C 235/46 |
| WO | 2015/061832 A1 | 5/2015 | |

OTHER PUBLICATIONS

Bahrami, Farnaz, et al., "p70 Ribosomal Protein S6 Kinase (Rps6kb1): an Update", J. Clin Pathol., 2014, pp. 1-7.
Bahrami, Farnaz, et al., "Monepantel Induces Autophagy in Human Ovarian Cancer Cells Through Disruption of the mTOR/p70S6K Signalling Pathway", Am. J. Cancer Res., 2014; vol. 4; No. 5; pp. 558-571.
Bahrami, Farnaz, et al., "Anticancer Properties of Novel Aminoacetonitrile Derivative Monepanel (ADD 1566) in Pre-Clinical Models of Human Ovarian Cancer", Am. J. Cancer Res., 2014; vol. 4; No. 5; pp. 545-557.
Lehrer, Steven, "Inhaled Biguanides and mTOR Inhibition for Influenza and Coronavirus (Review)", World Acad. Sci. J., 2020; vol. 2; No. 3; pp. 1-11.
Mislang, A., et al., "A preliminary assessment of oral monepantel's tolerability and pharmacokinetics in individuals with treatment-refractory solid tumors", Cancer Chemotherapy and Pharmacology, 2020; 86:589-594.

\* cited by examiner

*Primary Examiner* — Erich A Leeser
(74) *Attorney, Agent, or Firm* — ArentFox Schiff LLP; Daniel W. Clarke

(57) ABSTRACT

The present invention relates to the use of aminoacetonitrile derivatives (AADs) in the treatment of cancer and mTOR (mammalian Target of Rapamycin) pathway related diseases. In particular it relates to the use of AADs administered at particular dose amounts in order to achieve therapeutic effects.

12 Claims, 6 Drawing Sheets

USE OF AMINOACETONITRILE COMPOUNDS FOR THE TREATMENT OF INFECTION AND DISEASE

CROSS REFERENCE TO RELATED APPLICATIONS

The present application is a national stage application, filed under 35 U.S.C. § 371, of International Application No. PCT/AU2021/050435, filed May 11, 2021, which claims the benefit of priority to Australian provisional application No. 2020901514, filed on 11 May 2020; and to Australian provisional application No. 2020901776, filed on 29 May 2020 the entire contents of each of which are herein incorporated by reference.

FIELD

In general, the present invention relates to the use of aminoacetonitrile derivatives (AADs) in the treatment of cancer and mTOR (mammalian Target of Rapamycin) pathway related diseases. In particular it relates to the use of AADs administered at particular dose amounts in order to achieve therapeutic effects.

CROSS REFERENCE TO RELATED APPLICATIONS

The present application claims the benefit of priority to Australian provisional application No. 2020901514, filed on 11 May 2020; and to Australian provisional application No. 2020901776, filed on 29 May 2020 the entire contents of which is herein incorporated by reference.

BACKGROUND

Aminoacetonitrile derivatives (AADs) are a class of anthelmintics effective against drug-resistant nematodes. The nematodes, or roundworms, comprise a large number of pathogens of man and domestic animals. Gastrointestinal nematodes, such as Haemonchus contortus, are major parasites of ruminants that cause substantial economic losses to livestock production worldwide.

Monepantel (MPL) (N-[(1S)-1-Cyano-2-(5-cyano-2-trifluoromethyl-phenoxy)-1-methyl-ethyl]-4-trifluoromethyl-sulfanyl-benzamide) is an example of such an AAD and has been approved as a nematocide for the treatment of sheep gastrointestinal parasites.

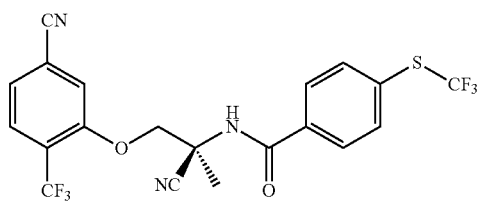

MPL

MPL has been shown to be efficacious against various species of livestock-pathogenic nematodes. MPL and various other AADs have also been shown to be effective in the treatment of cancer as well as in the treatment of a variety of diseases associated with the mTOR pathway.

Extensive safety/toxicology data generated to register MPL as an anthelmintic for livestock consumed by humans, demonstrates that monepantel is a very safe drug with minimal toxicity. Through a variety of in vivo studies in humans and animals, it has now been surprisingly found that MPL can be more effective in its anti-cancer activity and effects on mTOR pathway inhibition at lower doses as compared to higher doses.

Investigation of mTOR pathway inhibitors for the treatment of viral diseases has been undertaken and yielded mixed results. The newly identified severe acute respiratory coronavirus disease 2 (SARS-CoV-2), that originated in Wuhan, China, in December 2019, has quickly evolved as a rapidly developing pandemic named coronavirus disease 2019 (COVID-19). It has been declared a Public Health Emergency of International Concern by the World Health Organization. Various strategies for the treatment of COVID-19 are being considered and evaluated, however, the multifactorial morbidities associated with COVID-19 make the identification of a suitable drug candidate for the treatment of all patients an extremely difficult task. There is a substantial demand for treatments and vaccines, however, no definitive product is currently available. mTOR inhibition via rapamycin application has in fact been demonstrated to enhance the replicative activity/infectivity of SARS-CoV-2. Novel therapies are therefore required.

SUMMARY OF INVENTION

According to a first aspect the present invention provides a method for the treatment of cancer, or one or more mTOR pathway related diseases, the method comprising administering a therapeutically effective amount of a compound of formula (I):

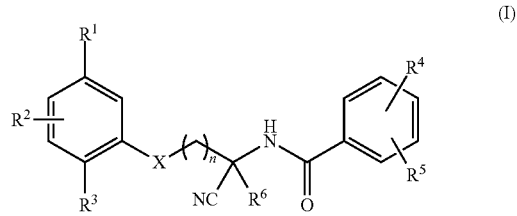

(I)

or a metabolite, pharmaceutically acceptable salt, solvate or prodrug thereof, to a patient in need thereof, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20;

wherein said therapeutically effective amount is an amount sufficient to achieve a plasma concentration of said compound and/or said metabolite of about 0.005 µM to about 15 µM.

According to a second aspect the present invention provides a compound of formula (I):

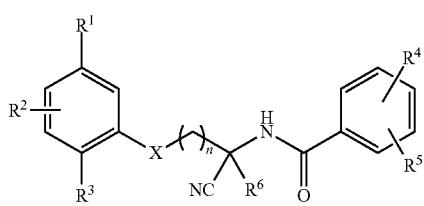
(I)

or a metabolite, pharmaceutically acceptable salt, solvate or prodrug thereof, for the treatment of cancer or one or more mTOR pathway related diseases in a subject, wherein, $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is a heteroatom, N(alkyl) or NH; and n is 1 to 20;

wherein treatment is to be carried out by administration of a therapeutically effective amount of said compound to the subject, wherein said therapeutically effective amount is an amount sufficient to achieve a plasma concentration of said compound and/or said metabolite of about 0.005 µM to about 15 µM.

According to a third aspect, the present invention provides use of a compound of formula (I):

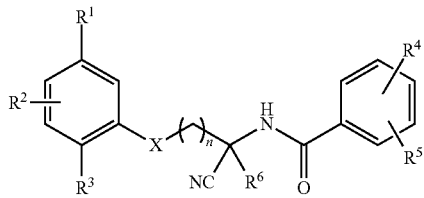
(I)

or a metabolite, pharmaceutically acceptable salt, solvate or prodrug thereof, for the manufacture of a medicament for the treatment of cancer or one or more mTOR pathway related diseases in a subject, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20;

wherein treatment is to be carried out by administration of a therapeutically effective amount of said compound to the subject, wherein said therapeutically effective amount is an amount sufficient to achieve a plasma concentration of said compound and/or said metabolite of about 0.2 µM to about 15 µM.

According to a fourth aspect, the present invention provides use of a compound of formula (I):

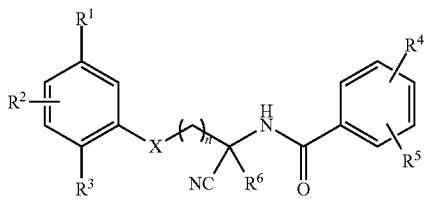
(I)

or a metabolite, pharmaceutically acceptable salt, solvate or prodrug thereof, for the manufacture of a medicament for the treatment of cancer or one or more mTOR pathway related diseases in a subject, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20;

wherein said medicament is formulated for administration of a therapeutically effective amount of said compound to the subject, wherein said therapeutically effective amount is an amount sufficient to achieve a plasma concentration of said compound and/or said metabolite of about 0.005 µM to about 15 µM.

According to a fifth aspect, the present invention provides a method for the treatment of coronavirus infection, the method comprising administering to a subject infected with coronavirus a therapeutically effective amount of a compound of formula (I):

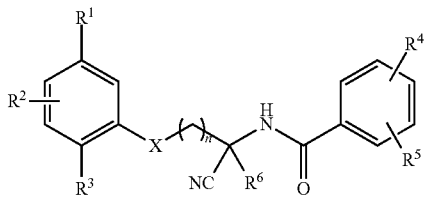
(I)

or a metabolite, pharmaceutically acceptable salt, solvate or prodrug thereof, to a patient in need thereof, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20.

According to a sixth aspect the present invention provides a compound of formula (I):

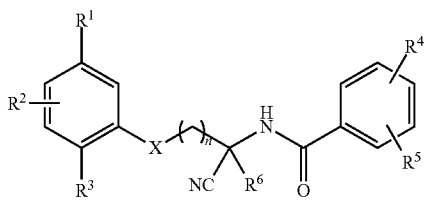
(I)

or a metabolite, pharmaceutically acceptable salt, solvate or prodrug thereof, for the treatment of coronavirus infection in a subject, wherein, $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is a heteroatom, N(alkyl) or NH; and n is 1 to 20.

According to a seventh aspect, the present invention provides use of a compound of formula (I):

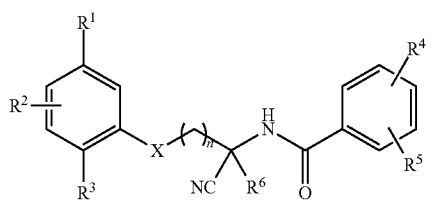

(I)

or a metabolite, pharmaceutically acceptable salt, solvate or prodrug thereof, for the manufacture of a medicament for the treatment of coronavirus infection in a subject, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20.

Preferably, $R^1$ is —CN, H or halogen. More preferably, $R^1$ is —CN. Preferably, $R^2$ is H or halogen, and more preferably H. Preferably, $R^3$ is —$CF_3$ or halogen and more preferably —$CF_3$. Preferably, $R^4$ is —$SCF_3$, —$SOCF_3$, —$SO_2CF_3$, —$OCF_3$ or —$CF_3$. More preferably, $R^4$ is —$SCF_3$ or —$SO_2CF_3$. Preferably, $R^5$ is H. Preferably, $R^6$ is alkyl and more preferably $CH_3$. Preferably, X is O. Preferably, n is 1 to 15, 1 to 10, 1 to 5, 1 to 2, or 1. Most preferably, n is 1. Preferably, $R^4$ is arranged para to the amide moiety.

The compound of formula (I) may be the (R)- or (S)-enantiomer or the racemate or a scalemic mixture. Preferably, the compound of formula (I) is the (S)-enantiomer.

The compound of formula (I) may be selected from any one of the following compounds:

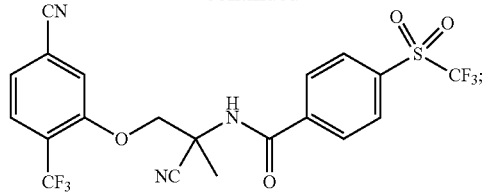

wherein each of the above compounds is the (R)- or (S)-enantiomer, or the racemate, or a metabolite, pharmaceutically acceptable salt, solvate or prodrug thereof.

Preferably, the compound of formula (I) may be selected from any one of the following compounds:

AAD 2224 (MPL-(R))

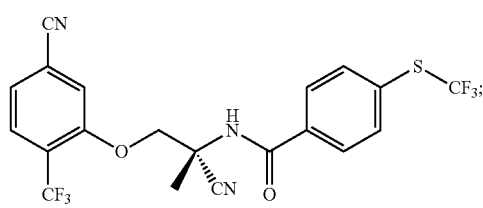

or a metabolite, pharmaceutically acceptable salt, solvate or prodrug thereof.

More preferably, the compound of formula (I) is MPL (N-[(1S)-1-cyano-2-(5-cyano trifluoromethyl-phenoxy)-1-methyl-ethyl]-4-trifluoromethylsulfanyl-benzamide):

MPL

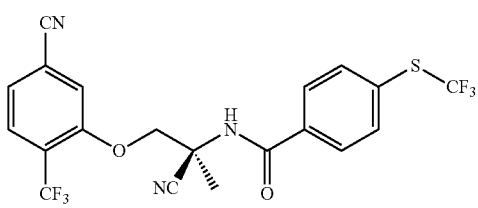

or a metabolite, pharmaceutically acceptable salt, solvate or prodrug thereof.

Further, the compound of the invention may be a metabolite of MPL, which is monepantel sulfone (MPL-$SO_2$):

MPL-$SO_2$

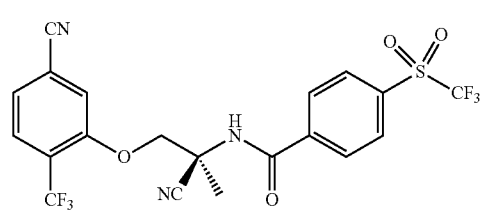

or a metabolite, pharmaceutically acceptable salt, solvate or prodrug thereof.

According to another aspect of the invention there is provided a method for the treatment of cancer, or one or more mTOR pathway related diseases in a subject, the method comprising administering a therapeutically effective amount of an AAD compound as described in PCT/JP2014/074764, or a metabolite thereof, wherein said therapeutically effective amount is an amount sufficient to achieve a plasma concentration of said compound and/or said metabolite of about 0.005 µM to about 15 µM.

According to another aspect of the invention there is provided a composition comprising an AAD compound as described in PCT/JP2014/074764, or a metabolite thereof, for the treatment of cancer, or one or more mTOR pathway related diseases in a subject, wherein the treatment is to be carried out by administration of a therapeutically effective amount of said compound to the subject, wherein said therapeutically effective amount is an amount sufficient to achieve a plasma concentration of said compound and/or said metabolite of about 0.005 µM to about 15 µM.

According to another aspect of the invention there is provided use of an AAD compound as described in PCT/JP2014/074764, or a metabolite thereof, in the manufacture of a medicament for the treatment of cancer, or one or more mTOR pathway related diseases in a subject, wherein said treatment is to be carried out by administration of a therapeutically effective amount of said compound to the subject, wherein said therapeutically effective amount is an amount sufficient to achieve a plasma concentration of said compound and/or said metabolite of about 0.005 µM to about 15 µM.

According to another aspect of the invention there is provided use of an AAD compound as described in PCT/JP2014/074764, or a metabolite thereof, in the manufacture of a medicament for the treatment of cancer, or one or more mTOR pathway related diseases in a subject, wherein said medicament is formulated for administration of a therapeutically effective amount of said compound to the subject, wherein said therapeutically effective amount is an amount sufficient to achieve a plasma concentration of said compound and/or said metabolite of about 0.005 µM to about 15 µM.

Preferably, the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Preferably, the cancer to be treated is selected from cancer of the ovaries, breast, prostate, mesothelioma cancer heamatopoietic, brain, esophageal, pancreatic and gastrointestinal, and most preferably the cancer to be treated is cancer of the ovaries.

Preferably, the one or more mTOR pathway related diseases is selected from Alzheimer's disease, Huntington's disease, motor neurone disease/amyotrophic lateral sclerosis, Parkinson's disease, age-related diseases, diseases related to transplant rejection, chronic inflammatory diseases, diseases related to glycogen storage, cancer, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, and fibrosis. Preferably, the mTOR pathway related disease is chronic inflammatory disease, which may be rheumatoid arthritis. Preferably, the fibrosis is fibrosis of the liver, cardiac fibrosis or pulmonary fibrosis. Most preferably the diseases to be treated are cancer and metastasis. Preferably, the cancer is associated with a kinase. Preferably, the kinase is a cyclin-dependent kinase, and more preferably, cdk2 or cdk4.

In another embodiment, the mTOR pathway related disease may be an effect of treatment for an mTOR pathway related disease. In a preferred embodiment the treatment for an mTOR pathway related disease is L-Dopa induced dyskinesia following/during treatment of Parkinson's Disease.

In another embodiment, the mTOR pathway related disease is a viral infection. In a preferred embodiment, the viral infection is infection with influenza virus, immunodeficiency virus or a coronavirus. In a preferred embodiment the infection is infection with a human T-lymphotrophic virus-1 (HTLV-1). In a preferred embodiment the infection is infection with a coronavirus selected from the four main Alpha-, Beta-, Gamma- and Deltacoronaviruses comprising: transmissible gastroenteritis virus (TGEV), porcine epidemic diarrhea virus (PEDV), porcine humagglutinating encephalomyelitis (PEHV), porcine respiratory coronavirus (PRCV), and human coronaviruses 229E and NL63 (HCoV-229E and HCoV-NL63), mouse hepatitis virus (MHV), bovine coronavirus-ENT strain (BCoV-ENT), bat-SL-CoVZC45, bat-SL-CoVZXC21, MERS-CoV, SARS-CoV and SARS-CoV-2, avian infectious bronchitis virus (IBV), avian bulbul coronavirus (Bulbus-CoV), and porcine coronavirus (PD-CoV). In a particularly preferred embodiment the viral infection is infection with SARS-CoV-2.

In another aspect the present invention provides a method for reducing or inhibiting the replication or infectivity of a virus in a cell comprising contacting the cell with a compound of Formula (I) as described in the aspects and embodiments herein above. In an embodiment the cell is in vivo. In another embodiment, the cell is in vitro. In a preferred embodiment, the virus is influenza, an immunodeficiency virus or a coronavirus. In a preferred embodiment the infection is an immunodeficiency virus such as human T-lymphotrophic virus-1 (HTLV-1). In a preferred embodiment the virus is a coronavirus selected from the four main Alpha-, Beta-, Gamma- and Deltacoronaviruses comprising: transmissible gastroenteritis virus (TGEV), porcine epidemic diarrhea virus (PEDV), porcine humagglutinating encephalomyelitis (PEHV), porcine respiratory coronavirus (PRCV), and human coronaviruses 229E and NL63 (HCoV-229E and HCoV-NL63), mouse hepatitis virus (MHV), bovine coronavirus-ENT strain (BCoV-ENT), bat-SL-CoVZC45, bat-SL-CoVZXC21, MERS-CoV, SARS-CoV and SARS-CoV-2, avian infectious bronchitis virus (IBV), avian bulbul coronavirus (Bulbus-CoV), and porcine coronavirus (PD-CoV). In a particularly preferred embodiment the virus is SARS-CoV-2.

In another aspect the present invention provides a compound of Formula (I) as described in the aspects and embodiments herein above for use in reducing or inhibiting the replication or infectivity of a virus in a cell. In an embodiment the cell is in vivo. In another embodiment, the cell is in vitro. In a preferred embodiment, the virus is influenza and immunodeficiency virus or a coronavirus. In a preferred embodiment the infection is an immunodeficiency virus such as human T-lymphotrophic virus-1 (HTLV-1). In a preferred embodiment the virus is a coronavirus selected from the four main Alpha-, Beta-, Gamma- and Deltacoronaviruses comprising: transmissible gastroenteritis virus (TGEV), porcine epidemic diarrhea virus (PEDV), porcine humagglutinating encephalomyelitis (PEHV), porcine respiratory coronavirus (PRCV), and human coronaviruses 229E and NL63 (HCoV-229E and HCoV-NL63), mouse hepatitis virus (MHV), bovine coronavirus-ENT strain (BCoV-ENT), bat-SL-CoVZC45, bat-SL-CoVZXC21, MERS-CoV, SARS-CoV and SARS-CoV-2, avian infectious bronchitis virus (IBV), avian bulbul coronavirus (Bulbus-CoV), and porcine coronavirus (PD-CoV). In a particularly preferred embodiment the virus is SARS-CoV-2.

In another aspect the present invention provides use of a compound of Formula (I) as described in the aspects and embodiments herein above in the manufacture of a medicament for reducing or inhibiting the replication or infectivity of a virus in a cell in a subject infected with said virus. In a preferred embodiment, the virus is influenza or a coronavirus. In a preferred embodiment the virus is a coronavirus selected from the four main Alpha-, Beta-, Gamma- and Deltacoronaviruses comprising: transmissible gastroenteritis virus (TGEV), porcine epidemic diarrhea virus (PEDV), porcine humagglutinating encephalomyelitis (PEHV), porcine respiratory coronavirus (PRCV), and human coronaviruses 229E and NL63 (HCoV-229E and HCoV-NL63), mouse hepatitis virus (MHV), bovine coronavirus-ENT strain (BCoV-ENT), bat-SL-CoVZC45, bat-SL-CoVZXC21, MERS-CoV, SARS-CoV and SARS-CoV-2, avian infectious bronchitis virus (IBV), avian bulbul coronavirus (Bulbus-CoV), and porcine coronavirus (PD-CoV). In a particularly preferred embodiment the virus is SARS-CoV-2.

Numbered Statements of Invention Follow:

1. A method for the treatment of cancer, or one or more mTOR pathway related diseases, the method comprising administering a therapeutically effective amount of a compound of formula (I):

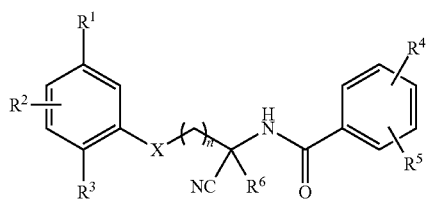

(I)

or a metabolite, pharmaceutically acceptable salt, solvate or prodrug thereof, to a patient in need thereof, wherein
$R^1$, $R^2$ and $R^3$ and $R^5$ are each independently selected from H, alkyl, halogen, —$CF_3$ or —CN;
$R^4$ and $R^6$ are each independently selected from H, alkyl, halogen, alkoxy, —$CF_3$, —$OCF_3$, —$SO_2CF_3$, —$SOCF_3$ or —$SCF_3$;
X is heteroatom, N(alkyl) or NH; and
n is 1 to 20;
wherein said therapeutically effective amount is an amount sufficient to achieve a plasma concentration of said compound and/or said metabolite of about 0.005 µM to about 15 µM.

2. The method according to statement 1, wherein,
$R^1$ is —CN, H or halogen;
$R^2$ is H or halogen;
$R^3$ is —$CF_3$ or halogen;
$R^4$ is —$SCF_3$, —$SOCF_3$, —$SO_2CF_3$, —$OCF_3$, or —$CF_3$;
$R^5$ is H;
$R^6$ is alkyl;
X is O; and
n is 1 to 5.

3. The method of statement 1 or 2, wherein R4 is para to the amide moiety.

4. The method of any one of statements 1 to 3, wherein the compound of formula (I) is the (R)- or (S)-enantiomer or the racemate.

5. The method of any one of statements 1 to 4, wherein the compound of formula (I) is the (S)-enantiomer.

6. The method statement 1, wherein the compound of formula (I) is selected from any one of the following compounds:

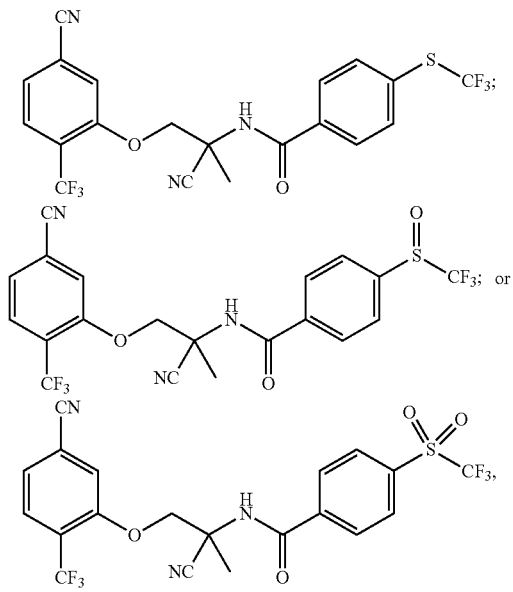

wherein each of the above compounds is the (R)- or (S)-enantiomer, or the racemate, or a metabolite, pharmaceutically acceptable salt, solvate or prodrug thereof.

7. The method of statement 6, wherein the compound of formula (I) is MPL (N-[(1R) cyano-2-(5-cyano-2-trifluoromethyl-phenoxy)-1-methyl-ethyl]-4-trifluoromethylsulfanyl-benzamide):

AAD 2224 (MPL-(R))

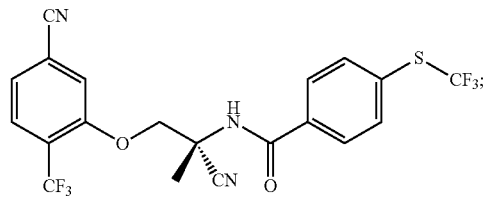

or a metabolite, pharmaceutically acceptable salt, solvate or prodrug thereof.

8. The method of statements 6, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

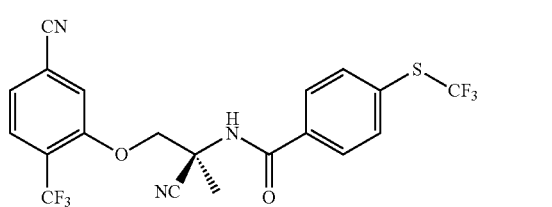

MPL or a metabolite, pharmaceutically acceptable salt, solvate or prodrug thereof.

9. The method of statement 6, wherein the compound of formula (I) is monepantel sulfone

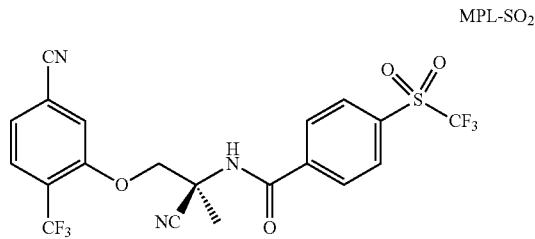 [SMILES: C[C@](C#N)(COc1cc(C#N)ccc1C(F)(F)F)NC(=O)c1ccc(S(=O)(=O)C(F)(F)F)cc1]

MPL-SO$_2$ or a metabolite, pharmaceutically acceptable salt, solvate or prodrug thereof.

10. The method according to any one of statements 1-9, wherein said compound is administered to achieve a plasma concentration of about 15 μM of said compound and/or said metabolite.

11. The method according to any one of statements 1-9, wherein said compound is administered to achieve a plasma concentration of about 10 μM of said compound and/or said metabolite.

12. The method according to any one of statements 1-9, wherein said compound is administered to achieve a plasma concentration of about 5 μM of said compound and/or said metabolite.

13. The method according to any one of statements 1-9, wherein said compound is administered to achieve a plasma concentration of about 1 μM of said compound and/or said metabolite.

14. The method according to any one of statements 1-9, wherein said compound is administered to achieve a plasma concentration of about 0.5 μM of said compound and/or said metabolite.

15. The method according to any one of statements 1-9, wherein said compound is administered to achieve a plasma concentration of about 0.2 μM of said compound and/or said metabolite.

16. The method of statement 1, wherein the compound according to formula (I) is MPL, and said therapeutically effective amount is an amount sufficient to achieve a plasma concentration of MPL-SO$_2$ of about 15 μM.

17. The method of statement 1, wherein the compound according to formula (I) is MPL, and said therapeutically effective amount is an amount sufficient to achieve a plasma concentration of MPL-SO$_2$ of about 10 μM.

18. The method of statement 1, wherein the compound according to formula (I) is MPL, and said therapeutically effective amount is an amount sufficient to achieve a plasma concentration of MPL-SO$_2$ of about 5 μM.

19. The method of statement 1, wherein the compound according to formula (I) is MPL, and said therapeutically effective amount is an amount sufficient to achieve a plasma concentration of MPL-SO$_2$ of about 1 μM.

20. The method of statement 1, wherein the compound according to formula (I) is MPL, and said therapeutically effective amount is an amount sufficient to achieve a plasma concentration of MPL-SO$_2$ of about 0.5 μM.

21. The method of statement 1, wherein the compound according to formula (I) is MPL, and said therapeutically effective amount is an amount sufficient to achieve a plasma concentration of MPL-SO$_2$ of about 0.2 μM.

22. The method according to any one of statements 1-21, wherein the compound is administered once daily.

23. The method according to any one of statements 1-21, wherein the compound is administered twice daily.

24. The method according to any one of statements 1-23, wherein the subject is a human.

25. The method according to any one of statements 1-23, wherein the subject is a non-human animal.

26. The method according to statement 25, wherein the non-human animal is a canine.

27. The method according to any one of statements 1-26, wherein the disease is cancer.

28. The method of statement 27, wherein the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

29. The method of any one of statements 1-24, wherein the one or more mTOR pathway related diseases is selected from Alzheimer's disease, Huntington's disease, motor neurone disease/amyotrophic lateral sclerosis, Parkinson's disease, age-related diseases, diseases related to transplant rejection, chronic inflammatory diseases, diseases related to glycogen storage, cancer, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, Parkinson's disease, fibrosis and viral infection.

30. A compound of formula (I):

(I)

or a metabolite, pharmaceutically acceptable salt, solvate or prodrug thereof, for the treatment of cancer or one or more mTOR pathway related diseases in a subject, wherein, $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is a heteroatom, N(alkyl) or NH; and n is 1 to 20;

wherein treatment is to be carried out by administration of a therapeutically effective amount of said compound to the subject, wherein said therapeutically effective amount is an amount sufficient to achieve a plasma concentration of said compound and/or said metabolite of about 0.005 µM to about 15 µM.

31. The compound according to statement 30, wherein, $R^1$ is —CN, H or halogen;

$R^2$ is H or halogen;

$R^3$ is —$CF_3$ or halogen;

$R^4$ is —$SCF_3$, —$SOCF_3$, —$SO_2CF_3$, —$OCF_3$, or —$CF_3$;

$R^5$ is H;

$R^6$ is alkyl;

X is O; and n is 1 to 5.

32. The compound of statement 30 or 31, wherein R4 is para to the amide moiety.

33. The compound of any one of statements 30 to 32, wherein the compound of formula (I) is the (R)- or (S)-enantiomer or the racemate.

34. The compound of any one of statements 30 to 33, wherein the compound of formula (I) is the (S)-enantiomer.

35. The compound statement 30, wherein the compound of formula (I) is selected from any one of the following compounds:

-continued wherein each of the above compounds is the (R)- or (S)-enantiomer, or the racemate, or a metabolite, pharmaceutically acceptable salt, solvate or prodrug thereof.

36. The compound of statement 35, wherein the compound of formula (I) is MPL (N-[(1R)-1-cyano-2-(5-cyano-2-trifluoromethyl-phenoxy)-1-methyl-ethyl]-4-trifluoromethylsulfanyl-benzamide):

AAD 2224 (MPL-(R))

or a metabolite, pharmaceutically acceptable salt, solvate or prodrug thereof.

37. The compound of statement 35, wherein the compound of formula (I) is MPL (N-[(1S) cyano-2-(5-cyano-2-trifluoromethyl-phenoxy)-1-methyl-ethyl]-4-trifluoromethylsulfanyl-benzamide):

MPL or a metabolite, pharmaceutically acceptable salt, solvate or prodrug thereof.

38. The compound of statement 35, wherein the compound of formula (I) is monepantel sulfone (MPL-$SO_2$):

MPL-$SO_2$ or a metabolite, pharmaceutically acceptable salt, solvate or prodrug thereof.

39. The compound according to any one of statements 30-38, wherein said compound is to be administered to achieve a plasma concentration of about 15 μM of said compound and/or said metabolite.
40. The compound according to any one of statements 30-38, wherein said compound is administered to achieve a plasma concentration of about 10 μM of said compound and/or said metabolite.
41. The compound according to any one of statements 30-38, wherein said compound is to be administered to achieve a plasma concentration of about 5 μM of said compound and/or said metabolite.
42. The compound according to any one of statements 30-38, wherein said compound is to be administered to achieve a plasma concentration of about 1 μM of said compound and/or said metabolite.
43. The compound according to any one of statements 30-38, wherein said compound is to be administered to achieve a plasma concentration of about 0.5 μM of said compound and/or said metabolite.
44. The compound according to any one of statements 30-38, wherein said compound is to be administered to achieve a plasma concentration of about 0.2 μM of said compound and/or said metabolite.
45. The compound of statement 30, wherein the compound according to formula (I) is MPL, and said therapeutically effective amount is an amount sufficient to achieve a plasma concentration of MPL-SO$_2$ of about 15 μM.
46. The compound of statement 30, wherein the compound according to formula (I) is MPL, and said therapeutically effective amount is an amount sufficient to achieve a plasma concentration of MPL-SO$_2$ of about 10 μM.
47. The compound of statement 30, wherein the compound according to formula (I) is MPL, and said therapeutically effective amount is an amount sufficient to achieve a plasma concentration of MPL-SO$_2$ of about 5 μM.
48. The compound of statement 30, wherein the compound according to formula (I) is MPL, and said therapeutically effective amount is an amount sufficient to achieve a plasma concentration of MPL-SO$_2$ of about 1 μM.
49. The compound of statement 30, wherein the compound according to formula (I) is MPL, and said therapeutically effective amount is an amount sufficient to achieve a plasma concentration of MPL-SO$_2$ of about 0.5 μM.
50. The compound of statement 30, wherein the compound according to formula (I) is MPL, and said therapeutically effective amount is an amount sufficient to achieve a plasma concentration of MPL-SO$_2$ of about 0.2 μM.
51. The compound according to any one of statements 30-50, wherein the compound is to be administered once daily.
52. The compound according to any one of statements 30-50, wherein the compound is to be administered twice daily.
53. The compound according to any one of statements 30-50, wherein the subject is a human.
54. The compound according to any one of statements 30-50, wherein the subject is a non-human animal.
55. The compound according to statement 54, wherein the non-human animal is a canine.
56. The compound according to any one of statements 30-55, wherein the disease is cancer.
57. The compound of statement 56, wherein the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.
58. The compound according to any one of statements 30-55, wherein the one or more mTOR pathway related diseases is selected from Alzheimer's disease, Huntington's disease, motor neuron diseases/amyotrophic lateral sclerosis, Parkinson's disease, age-related diseases, diseases related to transplant rejection, chronic inflammatory diseases, diseases related to glycogen storage, cancer, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, Parkinson's disease, fibrosis and viral infection.
59. The compound according to any one of statements 30-55, wherein the one or more the mTOR pathway related disease may be the treatment for an mTOR pathway related disease and is L-Dopa induced dyskinesia following treatment of Parkinson's disease.
60. The compound according to any one of statements 30-55, wherein the one or more the mTOR pathway related disease may be the treatment for an mTOR pathway related disease and is L-Dopa induced dyskinesia during treatment of Parkinson's disease.
61. Use of a compound of formula (I):

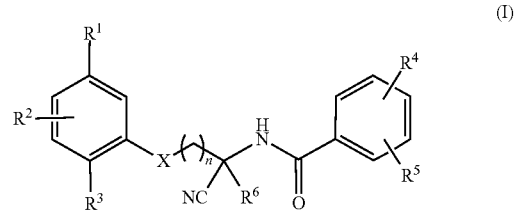

or a metabolite, pharmaceutically acceptable salt, solvate or prodrug thereof, for the manufacture of a medicament for the treatment of cancer or one or more mTOR pathway related diseases in a subject, wherein
$R^1$, $R^2$ and $R^3$ and $R^5$ are each independently selected from H, alkyl, halogen, —$CF_3$ or —CN;
$R^4$ and $R^6$ are each independently selected from H, alkyl, halogen, alkoxy, —$CF_3$, —$OCF_3$, —$SO_2CF_3$, —$SOCF_3$ or —$SCF_3$;
X is heteroatom, N(alkyl) or NH; and
n is 1 to 20;
wherein treatment is to be carried out by administration of a therapeutically effective amount of said compound to the subject, wherein said therapeutically effective amount is an amount sufficient to achieve a plasma concentration of said compound and/or said metabolite of about 0.005 μM to about 15 μM.

62. Use of a compound of formula (I):

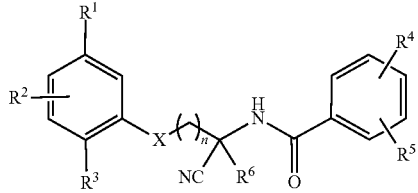

or a metabolite, pharmaceutically acceptable salt, solvate or prodrug thereof, for the manufacture of a medicament for the treatment of cancer or one or more mTOR pathway related diseases in a subject, wherein
$R^1$, $R^2$ and $R^3$ and $R^5$ are each independently selected from H, alkyl, halogen, —$CF_3$ or —CN;
$R^4$ and $R^6$ are each independently selected from H, alkyl, halogen, alkoxy, —$CF_3$, —$OCF_3$, —$SO_2CF_3$, —$SOCF_3$ or —$SCF_3$;
X is heteroatom, N(alkyl) or NH; and
n is 1 to 20;
wherein said medicament is formulated for administration of a therapeutically effective amount of said compound to the subject, wherein said therapeutically effective amount is an amount sufficient to achieve a plasma concentration of said compound and/or said metabolite of about 0.005 μM to about 15 μM.

63. The use of statement 61 or 62, wherein,
$R^1$ is —CN, H or halogen;
$R^2$ is H or halogen;
$R^3$ is —$CF_3$ or halogen;
$R^4$ is —$SCF_3$, —$SOCF_3$, —$SO_2CF_3$, —$OCF_3$, or —$CF_3$;
$R^5$ is H;
$R^6$ is alkyl;
X is O; and
n is 1 to 5.

64. The use of any one of statements 61-63, wherein R4 is para to the amide moiety.

65. The use of any one of statements 61-64, wherein the compound of formula (I) is the (R)- or (S)-enantiomer or the racemate.

66. The use of any one of statements 61-65, wherein the compound of formula (I) is the (S)-enantiomer.

67. The use of statement 61 or 62, wherein the compound of formula (I) is selected from any one of the following compounds:

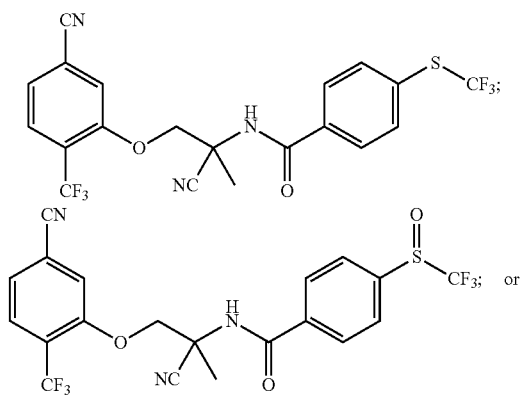

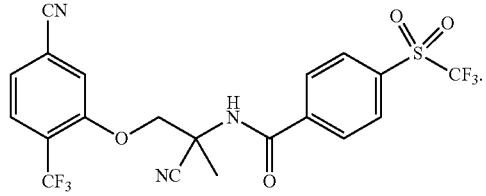

wherein each of the above compounds is the (R)- or (S)-enantiomer, or the racemate, or a metabolite, pharmaceutically acceptable salt, solvate or prodrug thereof.

68. The use of statement 67, wherein the compound of formula (I) is MPL (N-[(1R)-1-cyano-2-(5-cyano-2-trifluoromethyl-phenoxy)-1-methyl-ethyl]-4-trifluoromethylsulfanyl-benzamide):

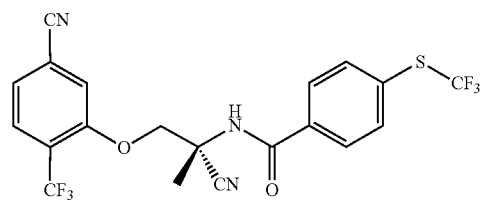

AAD 2224 (MPL-(R))

or a metabolite, pharmaceutically acceptable salt, solvate or prodrug thereof.

69. The use of statement 67, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

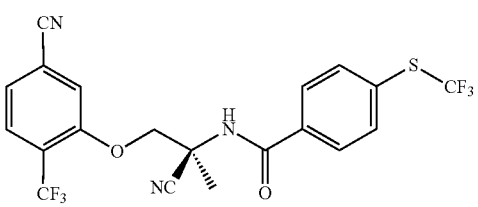

MPL or a metabolite, pharmaceutically acceptable salt, solvate or prodrug thereof.

70. The use of statement 67, wherein the compound of formula (I) is monepantel sulfone

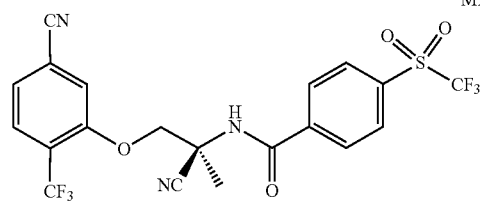

MPL-SO2 or a metabolite, pharmaceutically acceptable salt, solvate or prodrug thereof.

71. The use according to any one of statements 61-70, wherein said compound is to be administered to achieve a plasma concentration of about 15 µM of said compound and/or said metabolite.
72. The use according to any one of statements 61-70, wherein said compound is to be administered to achieve a plasma concentration of about 10 µM of said compound and/or said metabolite.
73. The use according to any one of statements 61-70, wherein said compound is to be administered to achieve a plasma concentration of about 5 µM of said compound and/or said metabolite.
74. The use according to any one of statements 61-70, wherein said compound is to be administered to achieve a plasma concentration of about 1 µM of said compound and/or said metabolite.
75. The use according to any one of statements 61-70, wherein said compound is to be administered to achieve a plasma concentration of about 0.5 µM of said compound and/or said metabolite.
76. The use according to any one of statements 61-70, wherein said compound is to be administered to achieve a plasma concentration of about 0.2 µM of said compound and/or said metabolite.
77. The use of statement 61 or 62, wherein the compound according to formula (I) is MPL, and said therapeutically effective amount is an amount sufficient to achieve a plasma concentration of MPL-SO$_2$ of about 15 µM.
78. The use of statement 61 or 62, wherein the compound according to formula (I) is MPL, and said therapeutically effective amount is an amount sufficient to achieve a plasma concentration of MPL-SO$_2$ of about 10 µM.
79. The use of statement 61 or 62, wherein the compound according to formula (I) is MPL, and said therapeutically effective amount is an amount sufficient to achieve a plasma concentration of MPL-SO$_2$ of about 5 µM.
80. The use of statement 61 or 62, wherein the compound according to formula (I) is MPL, and said therapeutically effective amount is an amount sufficient to achieve a plasma concentration of MPL-SO$_2$ of about 1 µM.
81. The use of statement 61 or 62, wherein the compound according to formula (I) is MPL, and said therapeutically effective amount is an amount sufficient to achieve a plasma concentration of MPL-SO$_2$ of about 0.5 µM.
82. The use of statement 61 or 62, wherein the compound according to formula (I) is MPL, and said therapeutically effective amount is an amount sufficient to achieve a plasma concentration of MPL-SO$_2$ of about 0.2 µM.
83. The use according to any one of statements 61-82, wherein the compound is formulated for administration once daily.
84. The use according to any one of statements 61-82, wherein the compound is formulated for administration once daily.
85. The use according to any one of statements 61-84, wherein the subject is a human.
86. The use according to any one of statements 61-84, wherein the subject is a non-human animal.
87. The use according to statement 86, wherein the non-human animal is a canine.
88. The use according to any one of statements 61-87, wherein the disease is cancer.
89. The use of statement 88, wherein the cancer is selected from the following: carcinoma, including that of the bladder, breast, colon, mesothelioma, kidney, liver, lung, including small cell lung cancer, non-small cell lung cancer, head and neck, oesophagus, gall bladder, ovary, pancreas, stomach, cervix, thyroid, prostate, and skin, including squamous cell carcinoma; hematopoietic tumors of lymphoid lineage, including leukaemia, acute lymphocytic leukaemia, acute lymphoblastic leukaemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocyte leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

90. The use of any one of statements 61-87, wherein the one or more mTOR pathway related diseases is selected from Alzheimer's disease, Huntington's disease, motor neurone disease/amyotrophic lateral sclerosis, Parkinson's disease, age-related diseases, diseases related to transplant rejection, chronic inflammatory diseases, diseases related to glycogen storage, cancer, metastasis, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, Parkinson's disease, fibrosis and viral infection.

91. The method of any one of statements 1-25, wherein the disease is coronavirus infection.

92. A method for the treatment of coronavirus infection, the method comprising administering to a subject infected with coronavirus a therapeutically effective amount of a compound of formula (I):

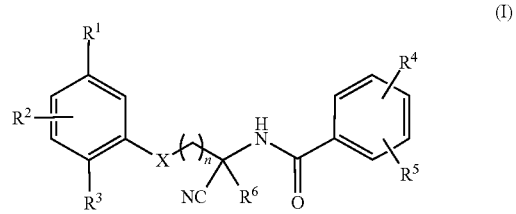

or a metabolite, pharmaceutically acceptable salt, solvate or prodrug thereof, to a patient in need thereof, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20.

93. A method for reducing or inhibiting the replication or infectivity of a virus in a cell comprising contacting the cell with a compound of Formula (I):

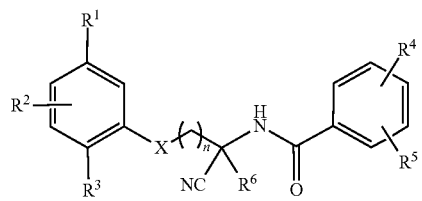

or a metabolite, pharmaceutically acceptable salt, solvate or prodrug thereof, to a patient in need thereof, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20.

94. The method of statement 92 or 93, wherein the compound of formula (I) is selected from any one of the following compounds:

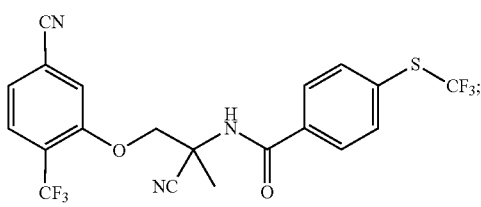

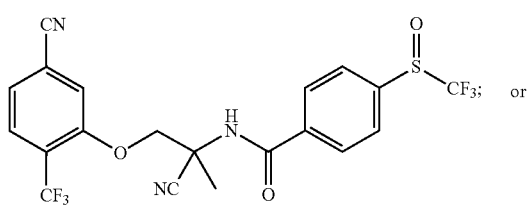

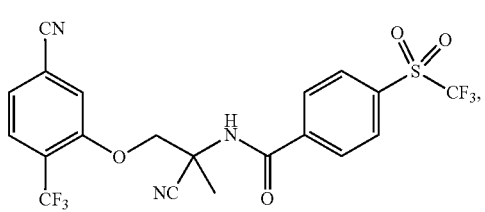

wherein each of the above compounds is the (R)- or (S)-enantiomer, or the racemate, or a metabolite, pharmaceutically acceptable salt, solvate or prodrug thereof.

95. The method of statement 94, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

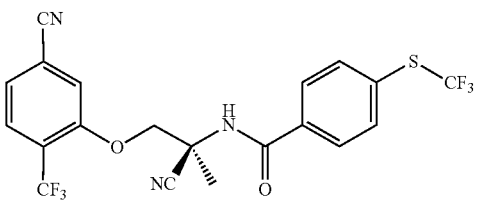

or a metabolite, pharmaceutically acceptable salt, solvate or prodrug thereof.

96. The method of any one of statements 91, 92, 94, or 95, wherein said coronavirus infection is infection with SARS-CoV-2.

97. The method of any one of statements 93-95, wherein the virus is coronavirus.

98. The method of statement 97, wherein the coronavirus is SARS-CoV-2.

99. The compound of any one of statements 30-54, wherein the disease is coronavirus infection.

100. A compound of formula (I):

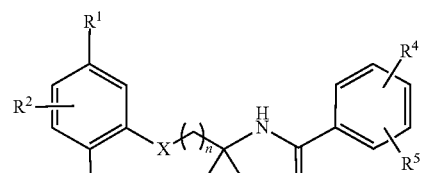

or a metabolite, pharmaceutically acceptable salt, solvate or prodrug thereof, for the treatment of coronavirus infection in a subject, wherein, $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is a heteroatom, N(alkyl) or NH; and n is 1 to 20.

101. A compound of Formula (I):

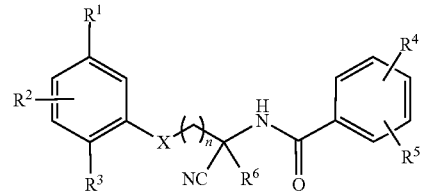

or a metabolite, pharmaceutically acceptable salt, solvate or prodrug thereof, for use in reducing or inhibiting the replication or infectivity of a virus in a cell, wherein, $R^1$, $R^2$ and $R^3$ and $R^5$ are each independently selected from H, alkyl, halogen, —$CF_3$ or —CN;

R⁴ and R⁶ are each independently selected from H, alkyl, halogen, alkoxy, —CF₃, —OCF₃, —SO₂CF₃, —SOCF₃ or —SCF₃;

X is a heteroatom, N(alkyl) or NH; and n is 1 to 20.

102. The compound of statement 100 or 101, wherein the compound of formula (I) is selected from any one of the following compounds:

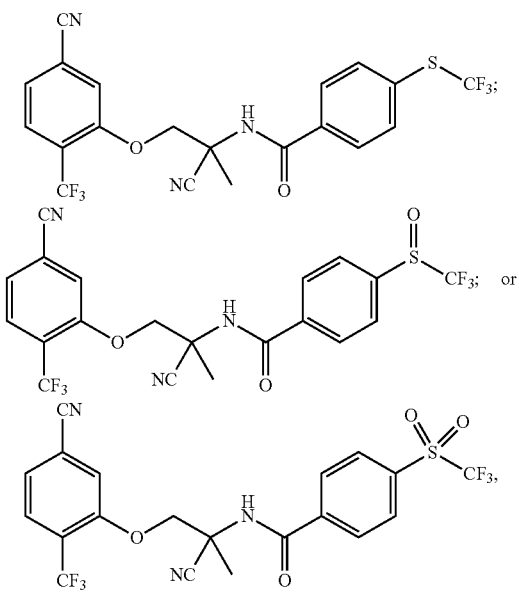

wherein each of the above compounds is the (R)- or (S)-enantiomer, or the racemate, or a metabolite, pharmaceutically acceptable salt, solvate or prodrug thereof.

103. The compound of statement 102, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

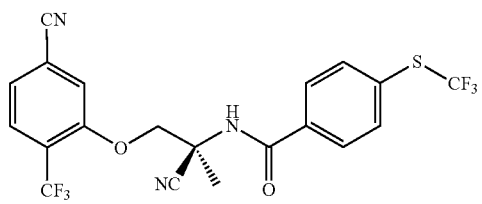

or a metabolite, pharmaceutically acceptable salt, solvate or prodrug thereof.

104. The compound of any one of statements 99, 100, 102 or 103, wherein said coronavirus infection is infection with SARS-CoV-2.

105. The compound of any one of statements 101-103, wherein the virus is coronavirus.

106. The compound of statement 105, wherein the coronavirus is SARS-CoV-2.

107. The use of any one of statements 61-86, wherein the disease is coronavirus infection.

108. Use of a compound of formula (I):

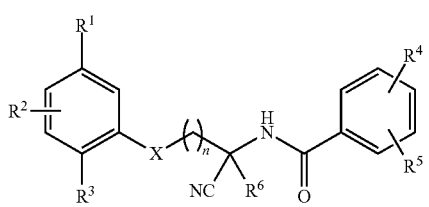

or a metabolite, pharmaceutically acceptable salt, solvate or prodrug thereof, for the manufacture of a medicament for the treatment of coronavirus infection in a subject, wherein R¹, R² and R³ and R⁵ are each independently selected from H, alkyl, halogen, —CF₃ or —CN;

R⁴ and R⁶ are each independently selected from H, alkyl, halogen, alkoxy, —CF₃, —OCF₃, —SO₂CF₃, —SOCF₃ or —SCF₃;

X is heteroatom, N(alkyl) or NH; and n is 1 to 20.

109. Use of a compound of Formula (I):

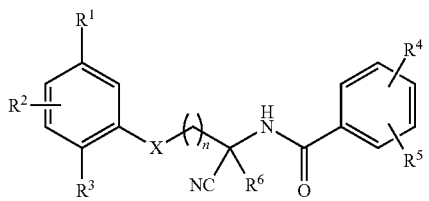

or a metabolite, pharmaceutically acceptable salt, solvate or prodrug thereof, for the manufacture of a medicament for reducing or inhibiting the replication or infectivity of a virus in a cell in a subject infected with said virus, wherein R¹, R² and R³ and R⁵ are each independently selected from H, alkyl, halogen, —CF₃ or —CN;

R⁴ and R⁶ are each independently selected from H, alkyl, halogen, alkoxy, —CF₃, —OCF₃, —SO₂CF₃, —SOCF₃ or —SCF₃;

X is heteroatom, N(alkyl) or NH; and n is 1 to 20.

110. The use of statement 108 or 109, wherein the compound of formula (I) is selected from any one of the following compounds:

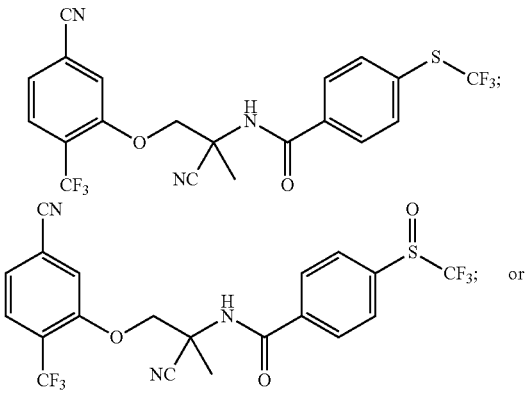

-continued

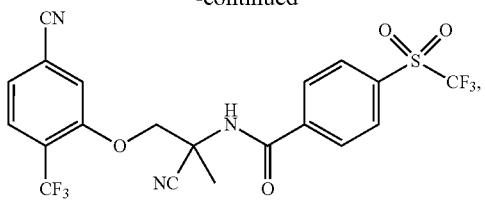

wherein each of the above compounds is the (R)- or (S)-enantiomer, or the racemate, or a metabolite, pharmaceutically acceptable salt, solvate or prodrug thereof.

111. The use of statement 110, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

MPL

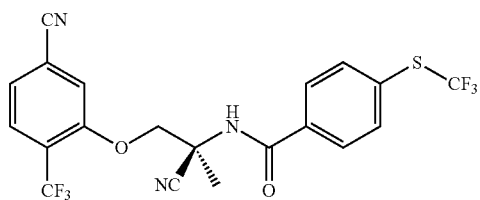

or a metabolite, pharmaceutically acceptable salt, solvate or prodrug thereof.

112. The use of any one of statements 107, 108, 110 or 111, wherein said coronavirus infection is infection with SARS-CoV-2.

113. The use of any one of statements 109-111, wherein the virus is coronavirus.

114. The compound of statement 113, wherein the coronavirus is SARS-CoV-2.

DEFINITIONS

Figure 1:
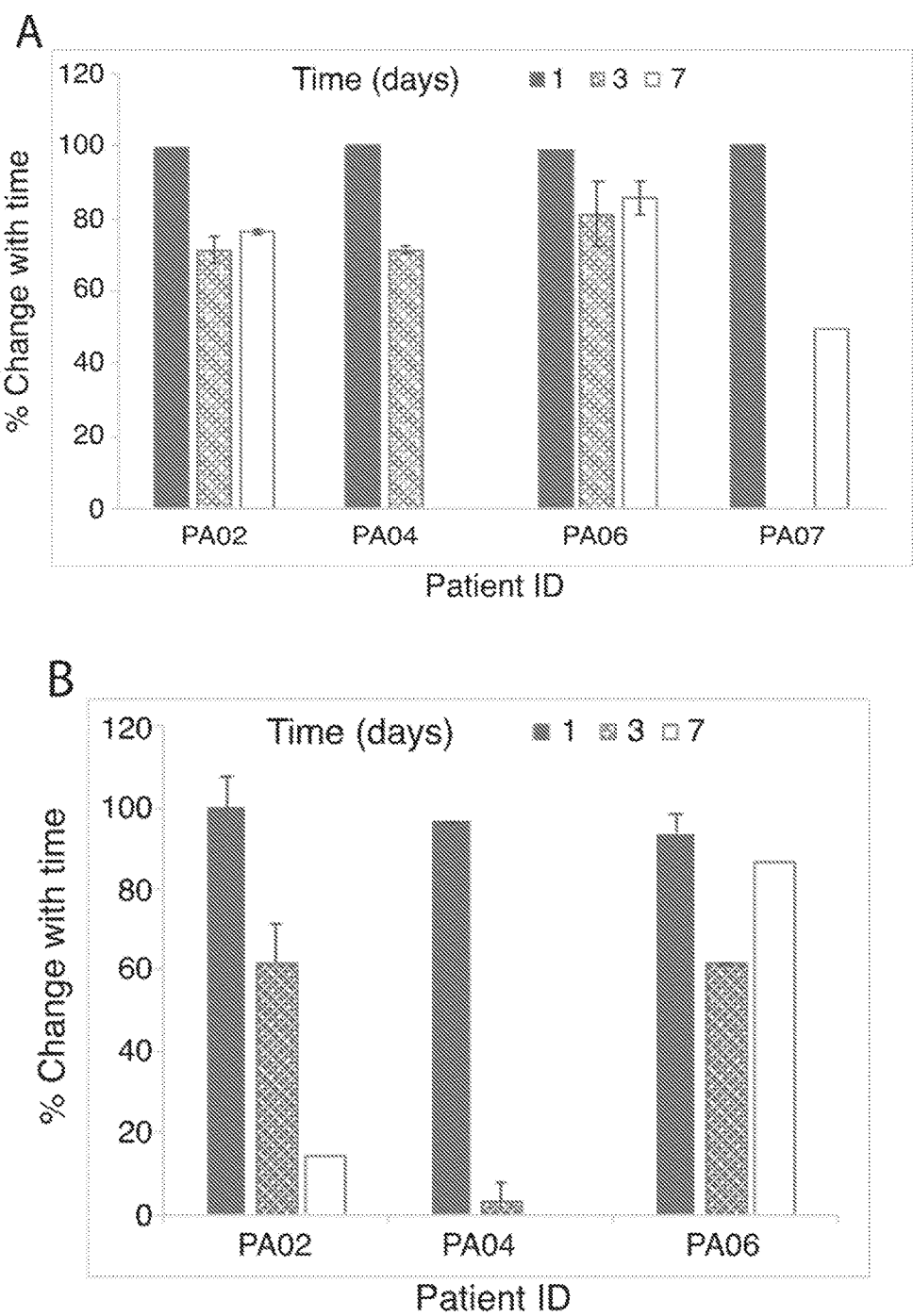
FIG. 1 shows phosphorylation levels of ribosomal protein S6 kinase beta-1 (RPS6KB1) (Panel A) or eurkaryotic translation initiation factor 4E-binding protein 1 (EIF-4EBP1) (Panel B) from preparations of peripheral blood mononuclear cells (PBMCs) obtained from patients treated with MPL (administered as Zolvix) daily at 5 mg/kg bw.

"Halogen" means fluorine, chlorine, bromine or iodine, preferably fluorine or chlorine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Aryl" by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl. The term "aryl" also includes fused cyclic hydrocarbon rings which are partially aromatic (i.e., one of the fused rings is aromatic and the other is non-aromatic). An exemplary aryl group which is partially aromatic is indanyl.

"Heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

"Heteroatom" means an atom selected from N, O, P and S. Where necessary, any undesignated valency is independently selected from H, OH, carbonyl, n-alkyl or alkoxy.

"n" may be 1 to 20, preferably 1 to 10, more preferably 1 to 6, and most preferably 1 to 4.

"Alkoxy" means an alkyl-O-group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options, meaning that more than one substituent may be present simultaneously at various sites.

"Prodrugs" and "solvates" of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of formula (I) or a metabolite, pharmaceutically acceptable salt or solvate of the compound. The transformation may occur by various mechanisms (e.g., by metabolic or chemical processes). A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

"Metabolites" of the compounds of the invention refer to the intermediates and products of metabolism.

The compounds of formula (I) may contain asymmetric or chiral centres, and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centres of the present invention can have the S or R configuration as defined by the IUPAC 1974.

The use of the terms "salt", "solvate", or "prodrug" and the like, is intended to equally apply to the salt, solvate and prodrug of enantiomers, stereoisomers, rotamers, tautomers, positional isomers, racemates or prodrugs of the inventive compounds.

As used in this application, the singular form "a", "an" and "the" include plural references unless the context clearly dictates otherwise.

As used herein, the term "comprising" means "including." Variations of the word "comprising", such as "comprise" and "comprises," have correspondingly varied meanings. Thus, for example, a pharmaceutical composition "comprising" a compound of formula (I) may consist exclusively of that compound or may include one or more additional components (e.g. a pharmaceutically acceptable carrier, excipient and/or diluent).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value).

The term "therapeutically effective amount" as used herein, includes within its meaning a non-toxic but sufficient amount of an agent or composition for use in the present invention to provide the desired therapeutic effect, which includes prevention of development of, or alleviation of the existing symptoms of, a target disease or condition, and/or prolong the survival. The exact amount required, including within any ranges specified, may vary from subject to subject depending on factors such as the species being treated, the age and general condition of the subject, the severity of the condition being treated, the particular agent being administered, the mode of administration and so forth. Thus, it is not possible to specify an exact "effective amount" applicable to all embodiments. However, for any given case, an appropriate "effective amount" may be determined by one of ordinary skill in the art using only routine experimentation.

As used herein, the terms "treatment," "treat," and "treating" refer to reversing, alleviating, inhibiting the progress of a disease or disorder as described herein, or delaying, eliminating or reducing the incidence or onset of a disorder or disease as described herein, as compared to that which would occur in the absence of the measure taken. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors, or in the context of viral infection, the subject may be determined to be infected with the virus but not displaying any symptoms). Treatment may also be continued after symptoms have resolved, for example to prevent or delay their recurrence.

DETAILED DESCRIPTION

The AADs (e.g. formula (I)) are a class of compounds that may be synthesized using the ordinary knowledge of organic synthetic methodology. For example, the AADs may be synthesised by derivitisation of phenols with chloroacetone, Strecker reaction and acylation of the resultant amine with aroyl chlorides (as shown in Scheme 1). Where necessary, a particular enantiomer may then be obtained, for example, by chiral resolution (as shown in Scheme 2).

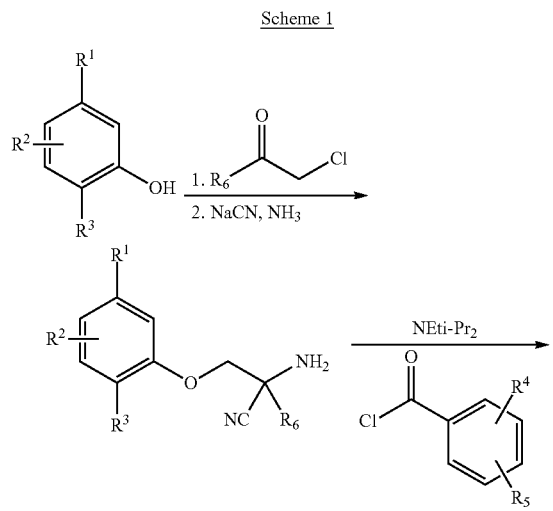

Scheme 1

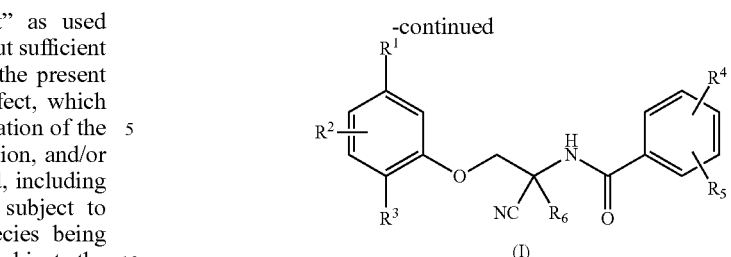

(I)

Scheme 2

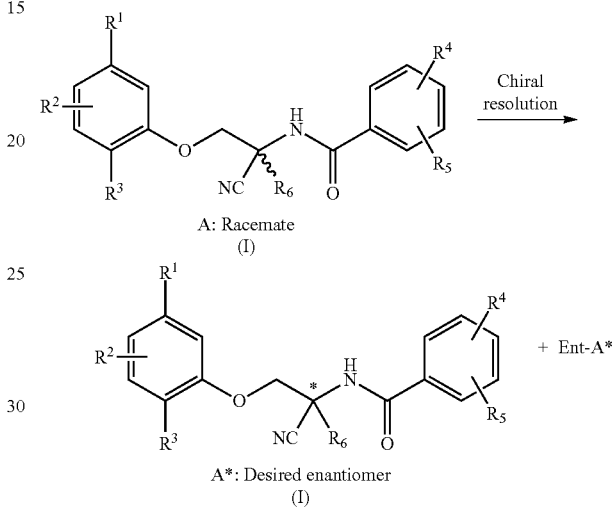

The AADs are a class of chemicals that have previously been used to treat drug-resistant nematodes. Research to date has focused on MPL targeting nicotinic acetyl choline receptors in nematodes, and has been used extensively for the treatment of parasites in ruminants.

The interaction of MPL with mammalian mTOR receptors may be selective for tumour cells causing inhibition of tumour growth Aminoacetonitrile derivatives including compounds of formula (I), such as MPL and MPL-SO$_2$, have been previously demonstrated to have anti-cancer activity. More specifically, compounds of formula (I), including MPL and MPL-SO$_2$, have been shown to inhibit mTOR signaling, which is typically up-regulated in cancer. However, the use of AADs for the treatment of a variety of diseases in addition to cancer has also been reported (see PCT/AU2013/000290, PCT/AU2013/000859, PCT/AU2014/001017, PCT/JP2014/074764 and PCT/JP2016/056514, which are incorporated herein by reference).

It has been surprisingly found by the inventors, that in subjects treated with the AAD monepantel, an inverse correlation between anti-cancer response and blood plasma levels of the AAD monepantel and monepantel sulfone (monepantel's major metabolite) was evident. Accordingly, the invention described herein is directed towards methods of administration and uses of AADs, in particular MPL, for the treatment of cancer and/or other mTOR pathway related diseases, involving low doses of the compound.

The inventors have surprisingly found that an anticancer effect can be achieved wherein a plasma concentration of an AAD (preferably MPL sulfone, the chief metabolite of the parent MPL, or the parent alone, or a combination of the parent and chief metabolite) of about 0.005 μNA to about 15 μNA is achieved. In a preferred embodiment the dose of AAD achieved in the plasma has a concentration of about 0.005 μNA to about 0.2 μM. In a preferred embodiment the dose of AAD achieved in the plasma has a concentration of about 0.2 μM to about 1 μM. In a preferred embodiment the dose of AAD achieved in the plasma has a concentration of about 1 μM to about 7 μM. In a preferred embodiment the dose of AAD achieved in the plasma has a concentration of about 7 μM to about 15 μM. In a preferred embodiment the dose of AAD achieved in the plasma has concentration of about 0.005 μM, about 0.01 μM, about 0.05 μM, about 0.1 μM, about 0.2 μM, about 0.3 μM, about 0.4 μM, about 0.5 μM, about 0.6 μM, about 0.7 μM, about 0.8 μM, about 0.9 μM, about 1 μM, about 2 μM, about 3 μM, about 4 μM, about 5 μM, about 6 μM, about 7 μM, about 8 μM, 9 μM, about 10 μM, about 11 μM, about 12 μM, about 13 μM, about 14 μM, or about 15 μM. In a preferred embodiment the dose of AAD achieves a plasma concentration of about 0.005 μM. In a preferred embodiment the dose of AAD achieves a plasma concentration of about 0.01 μM. In a preferred embodiment the dose of AAD achieves a plasma concentration of about 0.05 μM. In a preferred embodiment the dose of AAD achieves a plasma concentration of about 0.1 μM. In a preferred embodiment the dose of AAD achieves a plasma concentration of about 0.5 μM. In a preferred embodiment the dose of AAD achieves a plasma concentration of about 1 μM In a preferred embodiment the dose of AAD achieves a plasma concentration of about 5 μM In a preferred embodiment the dose of AAD achieves a plasma concentration of about 10 μM In a preferred embodiment the dose of AAD achieves a plasma concentration of about 15 μM In a preferred embodiment the dose of AAD achieved in the plasma represents a steady state trough concentration that is maintained for a period of longer than 24 h. In a preferred embodiment the dose of AAD achieved in the plasma represents a steady state trough concentration that is maintained for a period of 14 days. In a preferred embodiment the dose of AAD achieved in the plasma represents a steady state trough concentration that is maintained for a period of 28 days. In a preferred embodiment the dose of AAD achieved in the plasma represents a steady state trough concentration that is maintained for a period of longer than 28 days.

For example, a preferred dosage may be about 1-5 mg of the AAD per kg of body weight per 24 hours. Another preferred dosage may be a dose of up to 200 mg per kg of body weight per 24 hours. In a preferred embodiment, the dosing regimen may include a loading dose. Further, a preferred dosage may be about 5 mg of a compound of formula (I) per kg of body weight per 24 hours. In a preferred embodiment the dose of a compound of Formula (I) is about 5 mg per kg of body weight per 24 hours. In another preferred embodiment the dose of MPL is about 5 mg per kg of body weight per 24 hours. In another preferred embodiment the dose of MPL is about 10, 20, 30, 40, 50, 60, 70, 80, 90, 100, 110, 120, 130, 140, 150, 160, 170, 180 or 190 mg per kg of body weight per 24 hours. In another preferred embodiment the dose of MPL is about 200 mg per kg of body weight per 24 hours.

The modes and timing of administration required to obtain the desired plasma concentrations can be readily determined by one skilled in the art. For example, this may involve once, or twice daily administration, or administration of multiple doses per day or per week, or administration of a loading dose.

Viral Infection

As described hereinabove, the inventors have discovered that AADs can affect the mTOR pathway which is a central complex to a series of biochemical pathways that regulate autophagy and cell cycle replication in mammals. However, AADs and in particular MPL and its active metabolite, MPLS do not seem to have material toxicity which points away from their use in eukaryotic cell cycle regulation.

It has been surprisingly found that MPL and its metabolite MPL-Sulfone (MPLS) are useful for the treatment of the atypical flu COVID-19 resulting from infection by the virus SARS-CoV-2. As many antivirals including mTOR inhibitors demonstrate significant toxicity at preferred therapeutic doses, MPL and MPLS offer advantage due to minimal side effects whilst achieving an effective therapeutic low dose.

It is surprising that MPL and MPLS are effective in the treatment of viral infection as they lack the immunosuppressive activity of other mTOR inhibitors, e.g. Rapamycin (Sirolimus). Rapamycin has been considered as a potential therapeutic agent for treating COVID-19, (viral infection by SARS-CoV-2) however, mixed experimental outcomes, its toxicity and immunosuppressive properties contraindicate and limit its utility. Immunosuppression potentially inhibits the body's ability to mount an immunological response to the virus.

Under some conditions, mTOR targeting can act as a double-edged sword and participate in virion replication and virion release from cells.

The inventors have surprisingly shown activity of both MPL and MPLS as active/potent antiviral therapeutics in vitro. This observation lends itself to the use of AADs for the treatment of viral infections. In an embodiment, using active MPL as a primary treatment, it will be converted to a further active form (MPLS) in metabolic organs such as the liver, intestine and kidney, thus generating an effective therapy.

Although lung lesions have been considered as the major damage caused by SARS-CoV-2 infection, in severe cases, liver damage has also been reported. Similarly, previous studies have shown that liver damage was common in patients infected by SARS-CoV and MERS-CoV, and such damage was associated with the severity of the diseases. The first pass metabolism of MPL to MPLS in the liver may therefore materially improve therapeutic outcomes by local hepatic levels of MPLS.

SARS-CoV-2 shares close nucleic acid identity with the 2003 identified SARS-CoV (~79%); and the 2012 identified middle eastern respiratory syndrome-related coronavirus (MERS-CoV; ~50%. SARS-CoV-2, SARS-CoV and MERS-CoV, associate with more serious respiratory infections in humans while the alphacoronavirus members HCoV-229E and HCoV-NL63 associate with the common cold in humans. TGEV, PEDV, PEHV, BCoV-ENT, IBV, Bulbul-CoV and PD-CoV bear significant burden to the agricultural industry every year.

The invention thus provides compositions and methods for the treatment of a viral infection using the compounds herein described. In a preferred embodiment the virus is a coronavirus selected from the four main Alpha-, Beta-, Gamma- and Deltacoronaviruses comprising: transmissible gastroenteritis virus (TGEV), porcine epidemic diarrhea virus (PEDV), porcine humagglutinating encephalomyelitis (PEHV), porcine respiratory coronavirus (PRCV), and human coronaviruses 229E and NL63 (HCoV-229E and HCoV-NL63), mouse hepatitis virus (MHV), bovine coronavirus-ENT strain (BCoV-ENT), bat-SL-CoVZC45, bat-SL-CoVZXC21, MERS-CoV, SARS-CoV and SARS-CoV-2, avian infectious bronchitis virus (IBV), avian bulbul coronavirus (Bulbus-CoV), and porcine coronavirus (PD-CoV). In a particularly preferred embodiment the virus is SARS-CoV-2.

As described herein, lower MPL doses provide a higher antiviral activity towards SARS-CoV-2 than higher MPL doses. A biphasic antiviral response to MPL treatment is surprising and no cell toxicity is apparent at the lower end of the range. Reports already suggest that another mTOR inhibitor rapamycin may increase SARS-CoV-2 replicative activity/infectivity, so together with MPL's apparent biphasic mechanism of action, MPL treatment provides an advantage with respect to mTOR inhibition and SARS-CoV-2 infectivity. MPLS at higher doses shows a strong trend for antiviral activity, meaning that treatment with low dose MPL followed by metabolism to MPLS and somatic accumulation represents a viable therapeutic tool to combat SARS-CoV-2, and other viral infections.

Common symptoms of COVID-19 include fever, tiredness, dry cough. Other symptoms include shortness of breath, aches and pains, sore throat, diarrhea, nausea, or a runny nose. Less common symptoms include loss of taste or smell, and purple/blue lesions on feet and toes (COVID toes). It is envisaged that prevention or alleviation of these symptoms in subjects infected with SARS-CoV-2 may be achieved through administration of a therapeutically effective amount of an AAD, particularly MPL.

Typically, in treatment applications, the treatment may be for the duration of the disease, e.g. cancer, or duration of infection. Further, it will be apparent to one of ordinary skill in the art that the optimal quantity and spacing of individual dosages can be determined by the nature and extent of the disease state or condition being treated, the form, route and site of administration, and the nature of the particular subject being treated, including in the context of treatment with MPL, being cognizant of any accumulation of the sulfone (MPLS) over long periods of treatment. It will be apparent to the physician that dosing may need to be adjusted to take into account maintenance of target plasma levels. The assay of plasma monepantel and monepantel sulfone levels are easily developed and routine for a typical pathology/medical laboratory.

The inventors have surprisingly found that an antiviral effect can also be achieved with low concentrations of an AAD. In a preferred embodiment an antiviral effect is achieved using a dose of the AAD (preferably MPL sulfone, the chief metabolite of the parent MPL, or the parent alone, or a combination of the parent and chief metabolite) wherein a plasma concentration of about 0.005 µM to about 7 µM is achieved. In a preferred embodiment the dose of AAD achieved in the plasma has a concentration of about 0.005 µM to about 0.2 µM. In a preferred embodiment the dose of AAD achieved in the plasma has a concentration of about 0.2 µM to about 1 µM. In a preferred embodiment the dose of AAD achieved in the plasma has a concentration of about 0.05 µM to about 1.5 µM. In a preferred embodiment the dose of AAD achieved in the plasma has a concentration of about 1.5 µM to about 7 µM. In a preferred embodiment the dose of AAD achieved in the plasma has a concentration of about 7 µM to about 15 µM. In a preferred embodiment the dose of AAD achieved in the plasma has concentration of about 0.005 µM, 0.01 µM, 0.05 µM, 0.1 µM 0.2 µM, about 0.3 µM, about 0.4 µM, about 0.5 µM, about 0.6 µM, about 0.7 µM, about 0.8 µM, about 0.9 µM, about 1 µM, about 2 µM, about 3 µM, about 4 µM, about 5 µM, about 6 µM, about 7 µM, about 8 µM, about 9 µM about 10 µM or about 15 µM. In a preferred embodiment the dose of AAD achieves a plasma concentration of about 0.005 µM. In a preferred embodiment the dose of AAD achieves a plasma concentration of about 0.01 µM. In a preferred embodiment the dose of AAD achieves a plasma concentration of about 0.05 µM. In a preferred embodiment the dose of AAD achieves a plasma concentration of about 0.1 µM. In a preferred embodiment the dose of AAD achieves a plasma concentration of about 0.5 µM. In a preferred embodiment the dose of AAD achieves a plasma concentration of about 1 µM. In a preferred embodiment the dose of AAD achieves a plasma concentration of about 5 µM. In a preferred embodiment the dose of AAD achieves a plasma concentration of about 10 µM. In a preferred embodiment the dose of AAD achieves a plasma concentration of about 15 µM. In a preferred embodiment the dose of AAD achieved in the plasma represents a steady state trough concentration that is maintained for a period of longer than 24 h. In a preferred embodiment the dose of AAD achieved in the plasma represents a steady state trough concentration that is maintained for a period of 14 days. In a preferred embodiment the dose of AAD achieved in the plasma represents a steady state trough concentration that is maintained for a period of 28 days. In a preferred embodiment the dose of AAD achieved in the plasma represents a steady state trough concentration that is maintained for a period of longer than 28 days.

For example, a preferred dosage may be about 1-5 mg of the AAD per kg of body weight per 24 hours. Another preferred dosage may be a dose of up to 200 mg per kg of body weight per 24 hours. Further, a preferred dosage may be about 5 mg of a compound of formula (I) per kg of body weight per 24 hours. In a preferred embodiment the dose of a compound of Formula (I) is about 5 mg per kg of body weight per 24 hours. In another preferred embodiment the dose of MPL is about 5 mg per kg of body weight per 24 hours. In another preferred embodiment the dose of MPL is about 10, 20, 30, 40, 50, 60, 70, 80, 90, 100, 110, 120, 130, 140, 150, 160, 170, 180 or 190 mg per kg of body weight per 24 hours. In another preferred embodiment the dose of MPL is about 200 mg per kg of body weight per 24 hours.

The modes and timing of administration required to obtain the desired plasma concentrations can be readily determined by one skilled in the art. For example, this may involve once, or twice daily administration, or administration of multiple doses per day or per week, or administration of a loading dose.

Pharmaceutical Compositions and Modes of Administration

The present invention provides pharmaceutical compositions, medicaments and kits which comprise at least one compound of formula (I), or a metabolite, pharmaceutically acceptable salt, solvate or prodrug of said compound and at least one pharmaceutically acceptable carrier for use in the treatment of mTOR pathway related diseases. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pennsylvania.

Tablet preparations include micronisation of the active ingredient monepantel to reduce average particle size of 90% of all particles to a size of less than 10 µm. Tablet preparations include micronisation of the active ingredient monepantel to reduce average particle size of 90% of all particles to a size of less than 2 µm. Tablet preparations include micronisation of the active ingredient monepantel to reduce average particle size of 90% of all particles to a size of less than 1 µm. Tablet preparations include micronisation of the active ingredient monepantel to reduce average particle size of 90% of all particles to a size of less than 0.5 µm. Micronisation may also include comicronisation of tablet excipients, including detergent. A preferred detergent is sodium lauryl sulphate at a final tablet concentration of 1%, 2%, 5% or 10%. A preferred inclusion of sodium lauryl sulphate is at a final tablet concentration of 2%.

Liquid form preparations include solutions, suspensions and emulsions, for example water or water-propylene glycol solutions for parenteral injection or addition of sweeteners and opacifiers for oral solutions, suspensions and emulsions. Liquid form preparations may also include solutions for intranasal administration. The liquid form preparation may also include solutions for nebulization.

Aerosol preparations suitable for inhalation may include solutions and solids in powder form, which may be in combination with a pharmaceutically acceptable carrier, such as an inert compressed gas, e.g. nitrogen. Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably, the AAD (e.g. compound of formula (I) such as MPL) is administered orally.

Compositions and medicaments of the present invention may comprise a pharmaceutically acceptable carrier, adjuvant, excipient and/or diluent. The carriers, diluents, excipients and adjuvants must be "acceptable" in terms of being compatible with the other ingredients of the composition or medicament, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones and fumed silica; mineral oils such as liquid paraffin, soft paraffin or squalane; cellulose derivatives such as methyl cellulose, microcrystalline cellulose, ethyl cellulose, carboxymethylcellulose, sodium carboxymethylcellulose or hydroxylpropyl-methylcellulose; delta-polymorphic crystals such as Mannitol; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly; surfactants such as sodium lauryl sulphate, Ac-Di-Sol SD-711 croscarmellose sodium; and flow agents such as magnesium stearate. Typically, the carrier or carriers will form from about 10% to about 99.9% by weight of the composition or medicament.

Composition and medicaments of the present invention may be in a form suitable for administration by injection (e.g. for parenteral administration including subcutaneous, intramuscular or intravenous injection), by oral administration (such as capsules, tablets, caplets, and elixirs, for example), by topical administration (e.g. in the form of an ointment, cream or lotion, or a form suitable for delivery as an eye drop), or by intranasal inhalation (e.g. in the form of aerosols).

For administration as an injectable solution or suspension, non-toxic parenterally acceptable diluents or carriers can include, Ringer's solution, isotonic saline, phosphate buffered saline, ethanol and 1,2 propylene glycol. Methods for preparing parenterally administrable compositions and medicaments are apparent to those of ordinary skill in the art, and are described in more detail in, for example, Remington's Pharmaceutical Science, 15th ed., Mack Publishing Company, Easton, Pa.

For oral administration, some examples of suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose, microcrystalline cellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate, fumed silica, or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, mannitol, sodium oleate, sodium chloride or talc. Suitable time delay agents include glyceryl monostearate or glyceryl distearate. Suitable surfactants include SLS or Ac-Di-Sol SD-711 croscarmellose sodium.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or- laurate, polyoxyethylene sorbitan mono- or di-oleate, -stearate or- laurate and the like.

Formulations for oral administration may comprise one or more emulsifying agents. Suitable emulsifying agents include dispersing agents as exemplified above or natural gums such as guar gum, gum acacia or gum tragacanth.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

Compositions and medicaments of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions and medicaments of the present invention may be administered in the form of a liposome. Suitable methods to form liposomes are known in the art, and in relation to this specific reference is made to Prescott, (Ed), (1976), "Methods in Cell Biology", Volume XIV, Academic Press, New York, N.Y. p. 33 et seq.

Supplementary active ingredients such as adjuvants or biological response modifiers can also be incorporated into compositions and medicaments of the present invention.

Any suitable adjuvant may be included in compositions and medicaments of the present invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Other suitable adjuvants include Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminium salts such as aluminium hydroxide gel (alum) or aluminium phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; oil in water emulsions including those described in European Patent No. 0399843, U.S. Pat. No. 7,029,678 and PCT Publication No. WO 2007/006939; and/or additional cytokines, such as GM-CSF or interleukin-2, -7, or -12, granulocyte-macrophage colony-stimulating factor (GM-CSF), monophosphoryl lipid A (MPL), cholera toxin (CT) or its constituent subunit, heat labile enterotoxin (LT) or its constituent subunit, toll-like receptor ligand adjuvants such as lipopolysaccharide (LPS) and derivatives thereof (e.g. monophosphoryl lipid A and 3-Deacylated monophosphoryl lipid A), muramyl dipeptide (MDP) and F protein of Respiratory Syncytial Virus (RSV).

Subjects

Prophylactic and therapeutic methods of the present invention may be applied to any suitable subject. In some embodiments, the subject is a mammalian subject. For example, the subject may be a mouse, rat, dog, cat, cow, sheep, horse or any other mammal of social, economic or research importance. Hence, the subject may be a mammal such as, for example, a human or a non-human mammal.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

The present invention will now be described with reference to specific examples, which should not be construed as in any way limiting.

EXAMPLES

Example 1—Veterinary Study

In a Phase 2 veterinary clinical trial, monepantel was administered as tablets daily to six pet dog patients (dog identification numbers: 001-001, 001-002, 001-003, 003-001, 004-002 and 004-003) with treatment naïve B cell lymphoma at a target dose of 179 mg/kg bw. Superficial tumour lesions were measured with calipers, while lesions within the body were assessed by X-Ray, ultrasound, computer tomography (CT) and/or physical palpitation. Baseline Day 0 (D0) predose caliper, X-Ray, ultrasound and CT measurements where available as well as a complete physical examination were recorded.

Monepantel tablets administered daily at a target dose of 179 mg/kg bw to pet dogs with treatment naive B cell lymphoma resulted in a strong anti-cancer effect at D14. One dog achieved a partial response, four dogs achieved stable disease and one dog had progressive disease by RECIST 1.1 criteria (Table 1). At D28, a strong anticancer effect remained evident with four of four dogs achieving stable target superficial lymph node caliper measurements. At D28, one of these dogs had a previously unrecorded lesion by careful X-ray analysis and another dog had a palpable abdominal lesion, previously not palpable. These latter two dogs therefore were recorded as RECIST 1.1 progressive disease.

PA07) at 5 mg/kg bw provided an anticancer effect by computerised tomography (CT) scanning according to RECIST1.1 criteria. PA02, PA04 and PA06 all achieved RECIST1.1 stable disease by CT. PA07 had progressive disease. mTOR signalling was inhibited in all four patients by monepantel treatment as demonstrated by decreased phosphorylation levels of ribosomal protein S6 kinase beta-1 (RPS6KB1) from preparations of each individual's peripheral blood mononuclear cells (PBMCs; FIG. 1A). Evidence of mTOR pathway signalling inhibition in these patients was supported by the finding of decreased eurkaryotic translation initiation factor 4E-binding protein 1 (EIF-4EBP1) phosphorylation levels from the preparations of PBMCs from PA02, PA04 and PA06 (FIG. 1B). EIF-4EIBP1 phosphorylation levels were not assayed from preparations of PBMCs from PA07.

TABLE 1

RECIST 1.1 Tumour Response and Blood Plasma levels of pet dogs with treatment naive B cell lymphoma, treated with monepantel at a target dose of 179 mg/kg bw.

| | RECIST 1.1 TUMOUR RESPONSE | | | | BLOOD PLASMA | | | | | |
|---|---|---|---|---|---|---|---|---|---|---|
| | D14 | D28 | | | Monepantel ($\mu$M) | | | Monepantel sulfone ($\mu$M) | | |
| Dog ID | Target Lesions | Target Lesions | No X-Ray | Overall | Day 14 | Day 24 | Day 28 | Day 14 | Day 24 | Day 28 |
| 001-002 | PD | | | PD | 0.7 | | | 23.8 | | |
| 001-001 | SD | SD | PD | PD | 1.0 | 0.5 | 0.2 | 19.7 | 26.1 | 24.0 |
| 004-002 | SD | SD | SD | PD | 0.1 | | 0.1 | 7.4 | | 8.8 |
| 001-003 | SD | SD | SD | SD | 0.2 | | 0.3 | 9.0 | | 15.3 |
| 004-003 | SD | SD | SD | SD | 0.5 | | 0.1 | 13.1 | | 11.9 |
| 003-001 | PR | | | PR | 0.1 | | | 6.7 | | |

PR = partial response;
SD = stable disease;
PD = progressive disease;
Dog ID = Dog trial identification number.
No X-ray indicates RECIST 1.1 if no X-Ray measurements were included.

An inverse correlation between RECIST1.1 response and blood plasma levels of monepantel and monepantel sulfone was evident. The one dog (003-001) that achieved a partial response, recorded monepantel and monepantel blood plasma levels of 0.1 and 6.7 µM, respectively. The four dogs that achieved stable target lesion caliper measurements at day 28 recorded monepantel and monepantel blood plasma levels of 0.1 to 0.5 µM and 7.4 to 15.3 µM, respectively. The two dogs that recorded progressive disease by external measurement alone recorded monepantel and monepantel blood plasma levels of 0.2 to 1.0 µM and 19.7 to 26.1 µM respectively.

Example 2—Human Study

In a Phase 1 b clinical trial, monepantel administered as Zolvix daily to four human patients (PA02, PA04, PA06 and As shown in FIG. 1A, relative to pre-treatment, after three days of monepantel treatment, PA02, PA04 and PA06's PBMC RPS6KB1 phosphorylation levels were reduced by 27.3%, 28.6% and 81.2% respectively. After seven days of monepantel treatment, PA02, PA06 and PA07's PBMC RPS6KB1 phosphorylation levels were reduced by 85.6%. As shown in FIG. 1B, relative to pre-treatment, after three days of monepantel treatment, PA02, PA04 and PA06's PBMC EIF-4EBP1 phosphorylation levels were reduced by 38.5%, 96.6% and 34.4% respectively. After seven days of monepantel treatment, PA02's PBMC EIF-4EBP1 phosphorylation levels were reduced by 85.6%.

Blood plasma monepantel and monepantel sulfone levels of all four patients were recorded at intervals throughout treatment (Table 2).

TABLE 2

Blood plasma levels of monepantel and monepantel sulfone recorded at 0.25, 0.5, 1, 2, 4, 8, 12 and 24 hours (h) as well as pre-dose on days 3, 4, 5, 6, 7, 14, 21 and 28

| | Monepantel | | | | | | | |
|---|---|---|---|---|---|---|---|---|
| Patient | 0.25 h | 0.5 h | 1 h | 2 h | 4 h | 8 h | 12 h | 24 h |
| PA02 | 0 | 10.5 | 42.1 | 171 | 144 | 108 | 52.5 | 21.8 |
| PA04 | 12.2 | 31 | 61 | 112 | 187 | 40.2 | 18.6 | 9.95 |

TABLE 2-continued

Blood plasma levels of monepantel and monepantel sulfone recorded at 0.25, 0.5, 1, 2, 4, 8, 12 and 24 hours (h) as well as pre-dose on days 3, 4, 5, 6, 7, 14, 21 and 28

| | | | | | | | | |
|---|---|---|---|---|---|---|---|---|
| PA06 | 6.46 | 39.4 | 110 | 183 | 104 | 62.1 | 26.9 | 13.7 |
| PA07 | 0 | 16.1 | 46.2 | 99.1 | 234 | 63.6 | 24.1 | 11.6 |
| Average (ng/ml) | 4.7 | 24.3 | 64.8 | 141.3 | 167.3 | 68.5 | 30.5 | 14.3 |
| Average ($\infty$M) | 0.010 | 0.051 | 0.137 | 0.298 | 0.353 | 0.145 | 0.064 | 0.030 |

| Patient | D3 | D4 | D5 | D6 | D7 | D14 | D21 | D28 |
|---|---|---|---|---|---|---|---|---|
| PA02 | 16.4 | 14.7 | 9.94 | 9.99 | 7.42 | 4.85 | 4.34 | 4.65 |
| PA04 | 8.07 | 6.98 | 6.86 | 7.22 | 6.39 | 5.25 | | |
| PA06 | 9.99 | 8.65 | 5.72 | 4.62 | 4.58 | 3.23 | 3.16 | 2.96 |
| PA07 | 8.33 | 6.44 | 5.03 | 3.34 | 3.32 | | | |
| Average (ng/ml) | 10.7 | 9.2 | 6.9 | 6.3 | 5.4 | 4.4 | 3.8 | 3.8 |
| Average ($\infty$M) | 0.023 | 0.019 | 0.015 | 0.013 | 0.011 | 0.009 | 0.008 | 0.008 |

| | Monepantel Sulfone | | | | | | | |
|---|---|---|---|---|---|---|---|---|
| Patient | 0.25 h | 0.5 h | 1 h | 2 h | 4 h | 8 h | 12 h | 24 h |
| PA02 | 0 | 8.63 | 65.5 | 266 | 732 | 565 | 409 | 254 |
| PA04 | 5.4 | 37.5 | 152 | 482 | 1050 | 637 | 276 | 179 |
| PA06 | 0 | 32.1 | 252 | 639 | 663 | 398 | 348 | 258 |
| PA07 | 0 | 13.1 | 125 | 360 | 1140 | 689 | 351 | 214 |
| Average (ng/ml) | 1.4 | 22.8 | 148.6 | 436.8 | 896.3 | 572.3 | 346.0 | 226.3 |
| Average ($\infty$M) | 0.00 | 0.05 | 0.29 | 0.86 | 1.77 | 1.13 | 0.68 | 0.45 |

| Patient | D3 | D4 | D5 | D6 | D7 | D14 | D21 | D28 |
|---|---|---|---|---|---|---|---|---|
| PA02 | 269 | 291 | 233 | 232 | 215 | 158 | 157 | 180 |
| PA04 | 240 | 231 | 229 | 205 | 188 | 131 | | |
| PA06 | 285 | 276 | 250 | 216 | 235 | 154 | 146 | 162 |
| PA07 | 277 | 291 | 241 | 204 | 182 | 149 | 138 | 121 |
| Average (ng/ml) | 267.8 | 272.3 | 238.3 | 214.3 | 205.0 | 148.0 | 147.0 | 154.3 |
| Average ($\infty$M) | 0.53 | 0.54 | 0.47 | 0.42 | 10.41 | 0.29 | 0.29 | 0.31 |

Monepantel and monepantel sulfone pre-dose blood plasma trough levels from Day 3 of treatment for PA02, PA04 and PA06 were recorded to be in the range of 0.006 to 0.045 µM and 0.24 to 0.57 µM, respectively. Combined monepantel and monepantel sulfone pre-dose blood plasma trough levels from Day 3 of treatment for PA02, PA04 and PA06 were recorded to be in the range of 0.30 µM to 0.56 µM.

Example 3—MPL and MPLS Inhibition of SARS-COV-2 Infectivity

Method

VERO African green monkey kidney epithelial cells were infected with SARS-CoV-2 in the presence of fetal calf serum (FCS) (multiplicity of infection=0.01) according to standard protocols (Caly, L., et al., The FDA-approved drug ivermectin inhibits the replication of SARS-CoV-2 in vitro. Antiviral Res, 2020. 178: p. 104787). After 30 minutes, various concentrations of either monepantel or monepantel sulfone, diluted in DMSO, was added directly to the culture media, enabling analysis of each drug's effect upon secondary viral infection. DMSO concentrations in the media were kept constant at 0.1%. Cells were treated for 3 or 5 days as indicated.

VERO Cell Culture Lactate Dehydrogenase Levels (LDH) Following Infection with SARS-CoV-2

Figure 2:
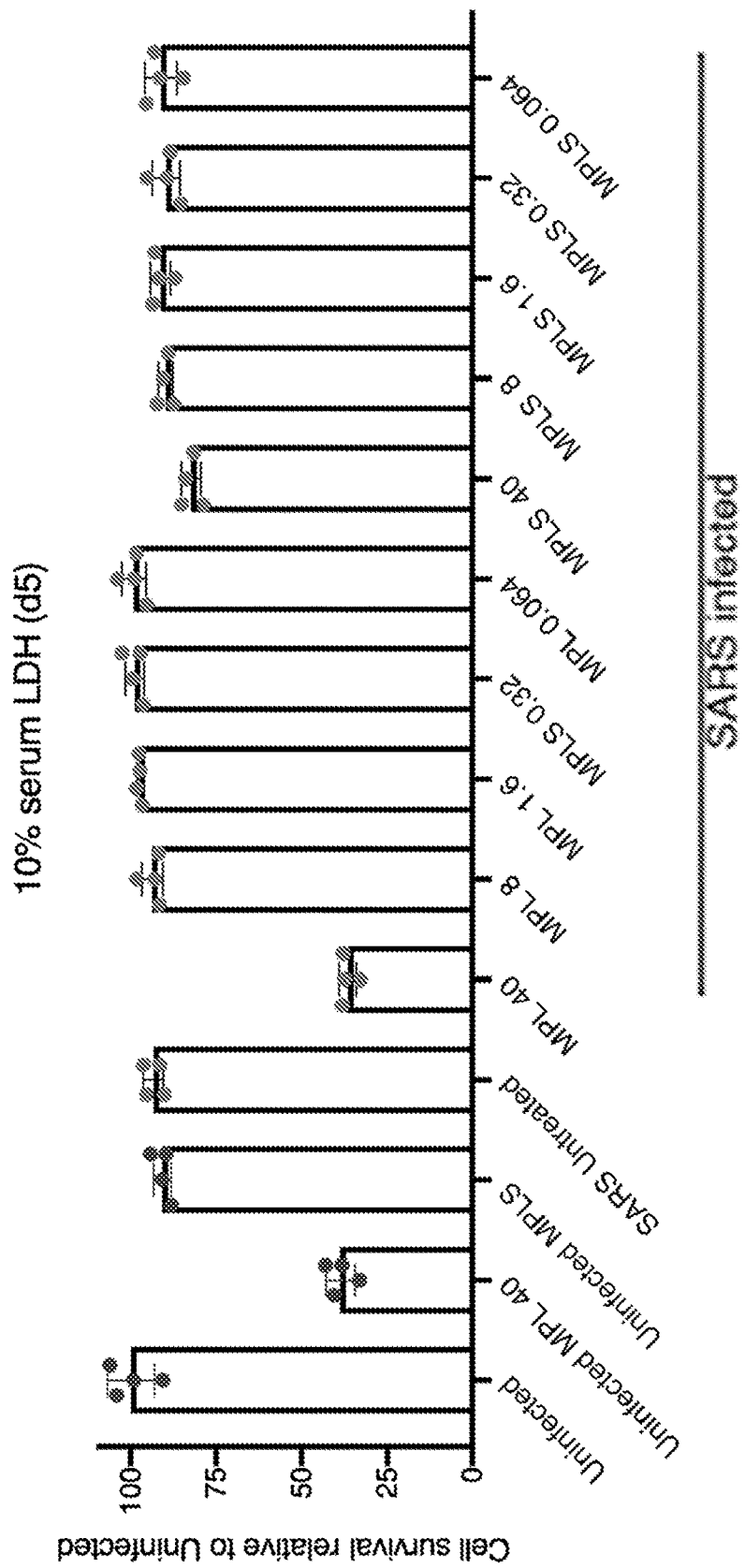
FIG. 2 shows a LDH assay of cultured VERO cells, infected with SARS-CoV-2 and treated with MPL or MPLS for five days. (Uninfected MoIS=Uninfected MoIS 40; MoIS=MPLS; X axis indicates relative concentration of MPL and MPLS in μM).

VERO cells were infected with SARS-CoV-2 and then treated with varying concentrations of MPL or MPLS (FIG. 2). Lactate dehydrogenase released into the medium was assayed as a measurement of cell death five days (d5) after infection/treatment according to standard protocols (Gassen, N.C., et al., SKP2 attenuates autophagy through Beclin1-ubiquitination and its inhibition reduces MERS-Coronavirus infection. Nat Commun, 2019. 10(1): p. 5770). Uninfected and/or untreated cell populations acted as controls. "Cell survival" (inverse) is displayed as proxy to cell death.

Vero cells either uninfected or infected with SARS-CoV-2 and then treated with 40 µM MPL display significant toxicity after five days of culture. Infection of cells in the absence of drug treatment did not show an apparent toxic effect. No additive effect of virus infection and MPL treatment was apparent and no apparent effect of lower MPL concentrations upon SARS-CoV-2 infected VERO cells was observed. It is not possible to accurately extrapolate an IC50 value for MPL here, however, considering the 8 µM and 40 µM values, one may estimate that the 1050=30 µM. This value is similar to that previously determined for immortalised CHO and HEK cells, but here in the presence of virus.

MPLS did not display a significant difference in terms of toxicity to uninfected and/or untreated controls at the concentrations tested here. MPLS alone, therefore, has a minimal toxic effect upon VERO cells infected with SARS-CoV-2 in the presence of 10% FCS over a five day culture period. CHO and cell 1050 values for MPLS treatment alone were 74 µM, and perhaps similar to MPLS levels here (HEK IC50 for MPLS treatment have not been determined).

SARS-CoV-2 infection alone increased cell death of VERO cells cultured in the absence of FCS compared to uninfected controls. Both MPL and MPLS alone show some toxicity to uninfected VERO cells when cultured in the absence of 10% FCS but only at relatively high concentrations. Following infection with SARS-CoV-2, treatment of VERO cells in the absence of FCS with MPL at 8 or 40 µM or MPLS at 40 µM appeared to increase toxicity caused by SARS-CoV-2 treatment. MPLS at 8 µM may slightly increase toxicity of VERO cells to SARS-CoV-2 infection under these conditions, but it does not appear to be significant. Concentrations of both MPL and MPLS below 8 µM showed no signs of toxicity to VERO cells.

In the presence of FCS, MPL at 8 to 0.064 µM does not apparently increase SARS-CoV-2 toxicity. MPLS at 40 to 0.064 µM does not apparently increase SARS-CoV-2 toxicity.

Figure 3:
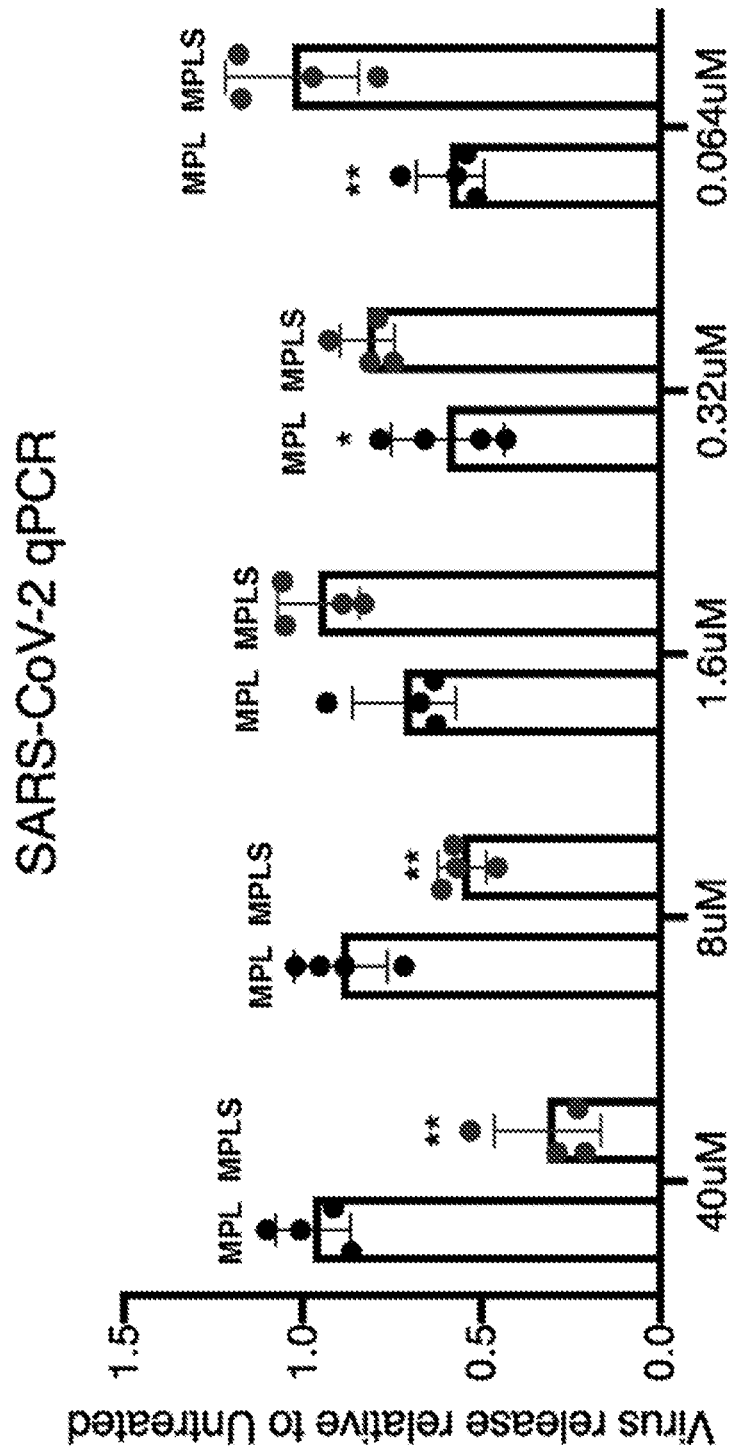
FIG. 3 shows LDH assay of cultured VERO cells, infected with SARS-CoV-2 and treated with MPL or MPLS for five days. (Uninfected MoIS=Uninfected MoIS 40; MoIS=MPLS; X axis indicates relative concentration of MPL and MPLS in μM).

Quantitative PCR (qPCR) was employed to determine the quantity of viral RNA in VERO cell cultures following infection with SARS-CoV-2 and then treatment with either MPL or MPLS at varying concentrations according to standard protocols (FIG. 3; Caly, L., et al., The FDA-approved drug ivermectin inhibits the replication of SARS-CoV-2 in vitro. Antiviral Res, 2020. 178: p. 104787.). Values are normalised to control untreated and infected cell values. Lower concentrations of MPL significantly decrease SARS-CoV-2 RNA concentrations in the media (both 0.032 µM and 0.064 µM MPL values were significantly reduced compared to 40 µM and 8 µM values p<0.05 and <0.001, respectively, ANOVA and Tukey post hoc tests). Conversely, higher concentrations of MPLS significantly decreased in SARS-CoV-2 RNA concentration in the media (both 40 µM and 8 µM MPL values were significantly reduced compared to 0.064 µM, p<0.001, ANOVA and Tukey post hoc tests). Therefore, despite MPL and MPLS having apparently no significant toxicity to cells at 0.064 and 0.032 µM and 8 µM, respectively, SARS-CoV-2 RNA in the culture media is significantly reduced. This suggests that MPL and MPLS are having a direct effect upon the inhibition of virus RNA replication.

SARS-CoV-2 Infectious Particle Concentrations in VERO Cell Culture Media

Figure 4:
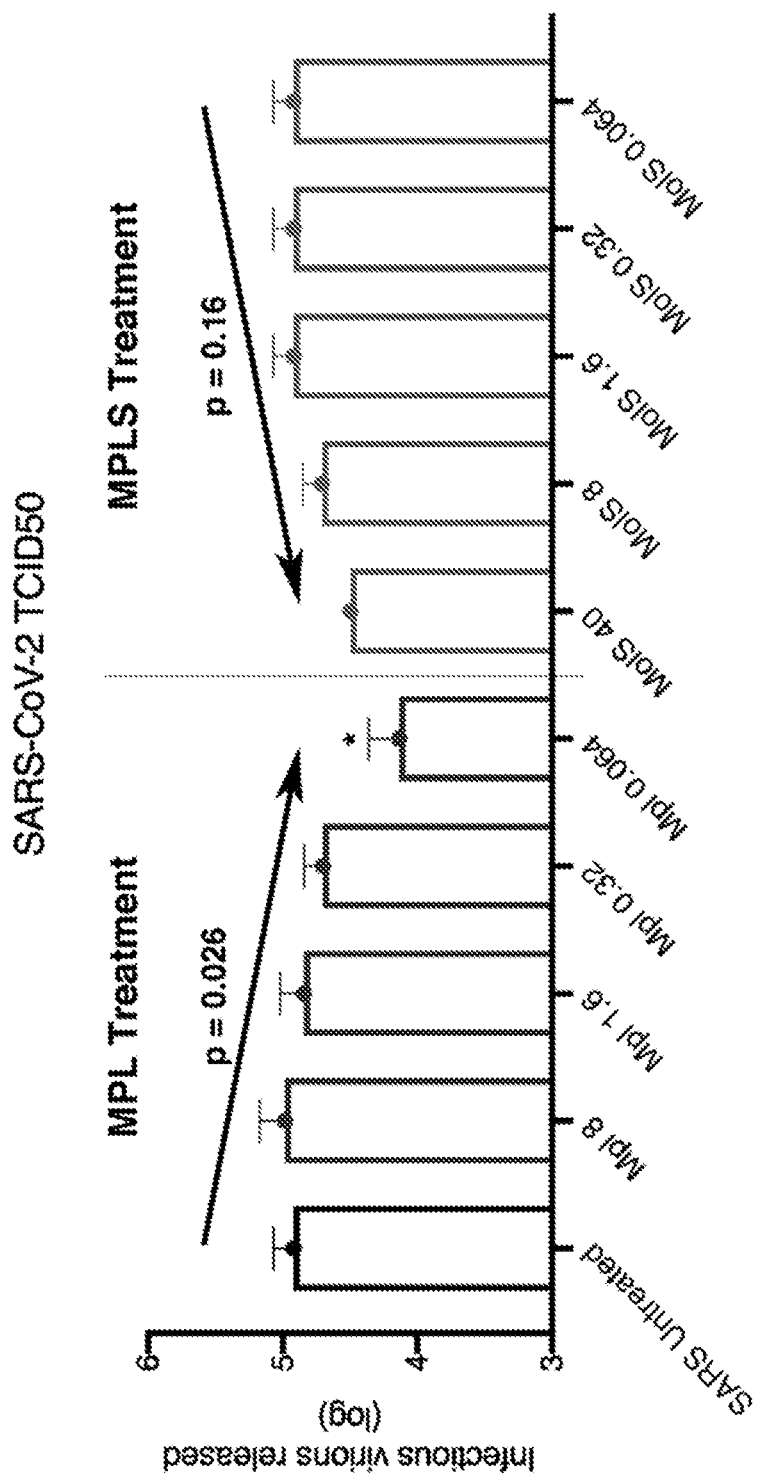
FIG. 4 shows TCID50 levels of SARS-CoV-2 following secondary infection of VERO cells in the presence of MPL or MPLS. Values along the X axis are expressed as μM of the original culture concentrations (one way ANOVA, p=0.026; Dunnett's post hoc test, p=0.045; SARS Untreated=84 000+/−34 000 virions vs Mpl 0.064 μM 13 700+/−9 420 virions; * p<0.05).

Although both MPL and MPLS reduce SARS-CoV-2 RNA in the media, it is not known whether this RNA is infectious, that is whether it has been efficiently packaged for viable subsequent and secondary infection. Serial dilutions of SARS-CoV-2 infected media from the range of MPL and MPLS concentrations tested above were added to fresh VERO cells cultured and median tissue culture infectious dose (TCID50) values were determined (FIG. 4; see standard protocols (Guo, L., et al., Autophagy Negatively Regulates Transmissible Gastroenteritis Virus Replication. Sci Rep, 2016. 6: p. 23864). MPL at 40 µM was not tested as cell death at this level was considered relatively high for this test. TCID50s values were calculated as relative infectious virions released.

MPL treatment significantly reduces SARS-CoV-2 secondary infectivity. At a concentration of 0.064 µM, monepantel treatment significantly reduces SARS-CoV-2 infectivity compared to no treatment. Concentrations of 0.32, 1.6 and 8.0 µM MPL did not significantly reduce SARS-CoV-2 in this assay. Both 8 and 40 µM MPLS treatment reduce the pathogenicity of VERO cell culture media following infection with SARS-CoV-2. A strong trend for MPLS treatment in the inhibition of SARS-CoV-2 infectivity is apparent. It can therefore be interpreted from this TCID50 assay that treatment with either MPL or MPLS reduces the capacity of SARS-CoV-2 to produce infectious virions.

Figure 5:
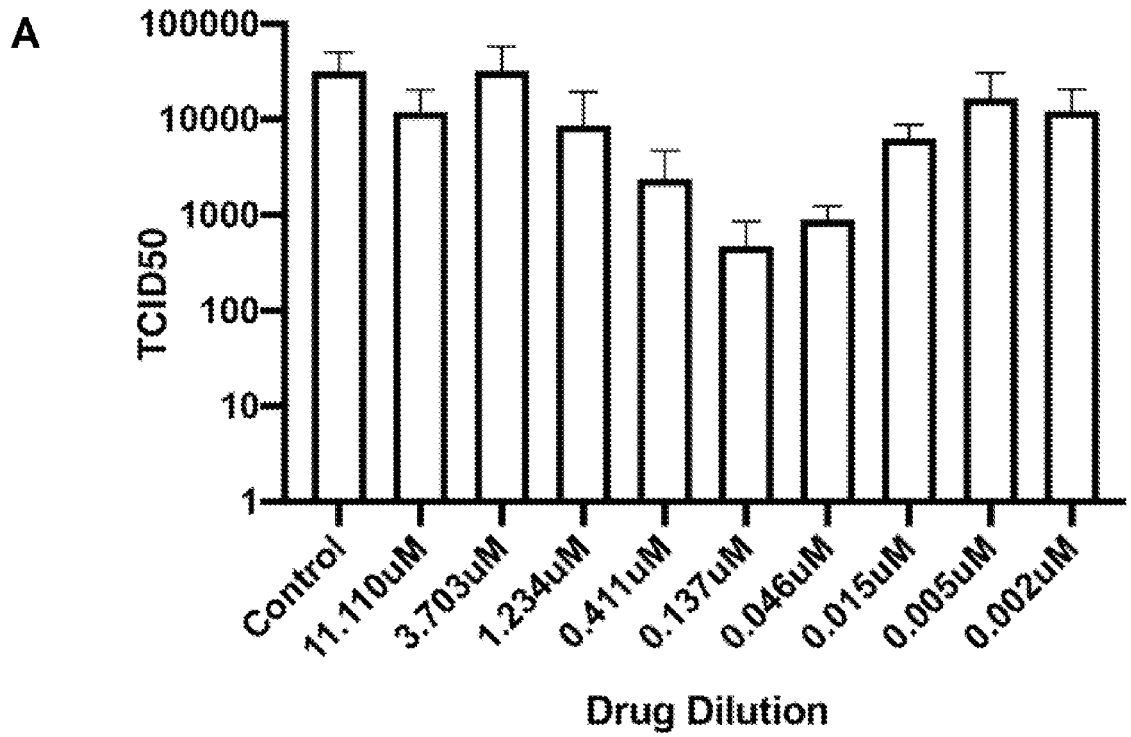
FIG. 5 shows a repeat experiment of the TCID50 levels of SARS-CoV-2 following secondary infection of VERO cells in the presence of either MPL (A) or MPLS (B). Values along the X axis are expressed as μM of the original culture concentrations. TCID 50 data calculated represent an aggregated score from the experimental wells and dilutions taking into account wells where a cell pathological effect was observed versus wells where no cell pathological effect was observed. Scores were created using the Spearman and Karber algorithm in Microsoft®Excel9R) and provided as means+/−standard deviation.
Figure 5:
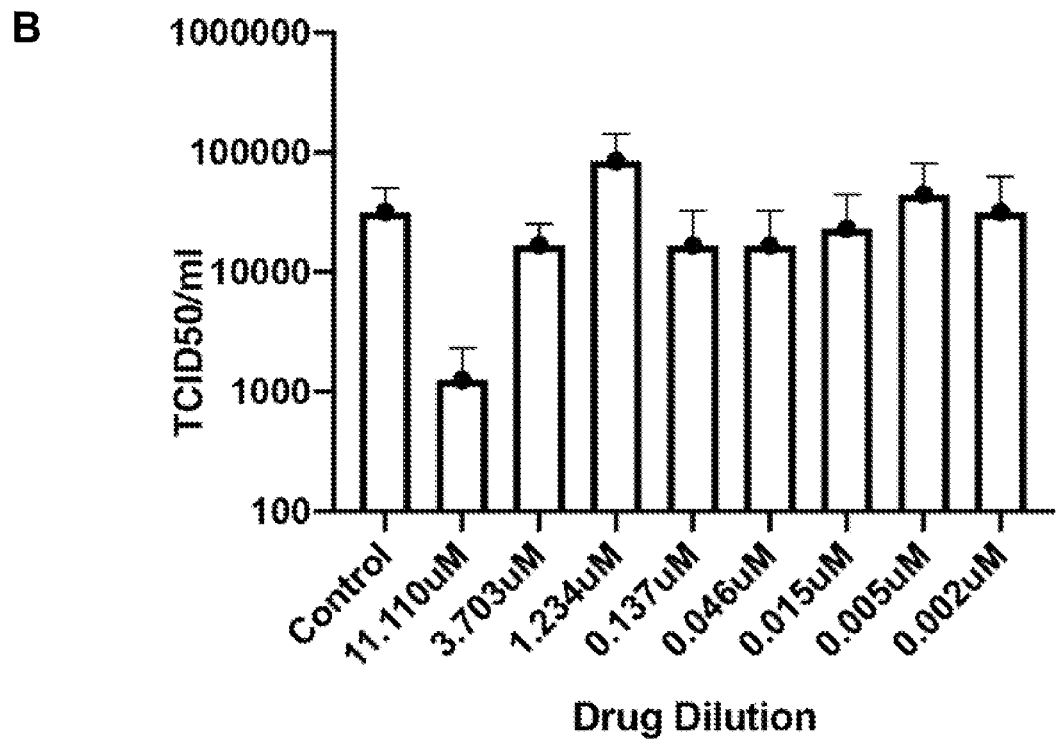

In a repeat experiment testing the TCID50 of MPL and MPLS upon VERO cells infected with SARS-CoV-2, a similar result was obtained (FIG. 5). A greater titration was used and data show that 0.137 µM MPL significantly reduces SARS-CoV-2 infectivity compared to no treatment. Concentrations of 0.411 µM and 0.046 µM MPL also significantly reduced SARS-CoV-2 infectivity, with the greatest effect observed at 0.137 µM. The highest concentration of MPLS, 11.11 µM significantly reduces SARS-CoV-2 infectivity compared to no treatment. It can therefore be interpreted from this repeat TCID50 assay that treatment with either MPL or MPLS reduces the capacity of SARS-CoV-2 to produce infectious virions.

In a repeat experiment testing the TCID50 of MPL and MPLS upon Calu-3 human cells infected with SARS-CoV-2, a similar result was again obtained wherein MPL and MPLS reduced SARS-CoV-2 infectivity at concentrations ranging from 3.00 µM down to 0.013 µM. It can therefore be interpreted from this TCID50 assay that treatment with either MPL or MPLS reduces the capacity of SARS-CoV-2 to produce infectious virions in human cells.

Figure 6:
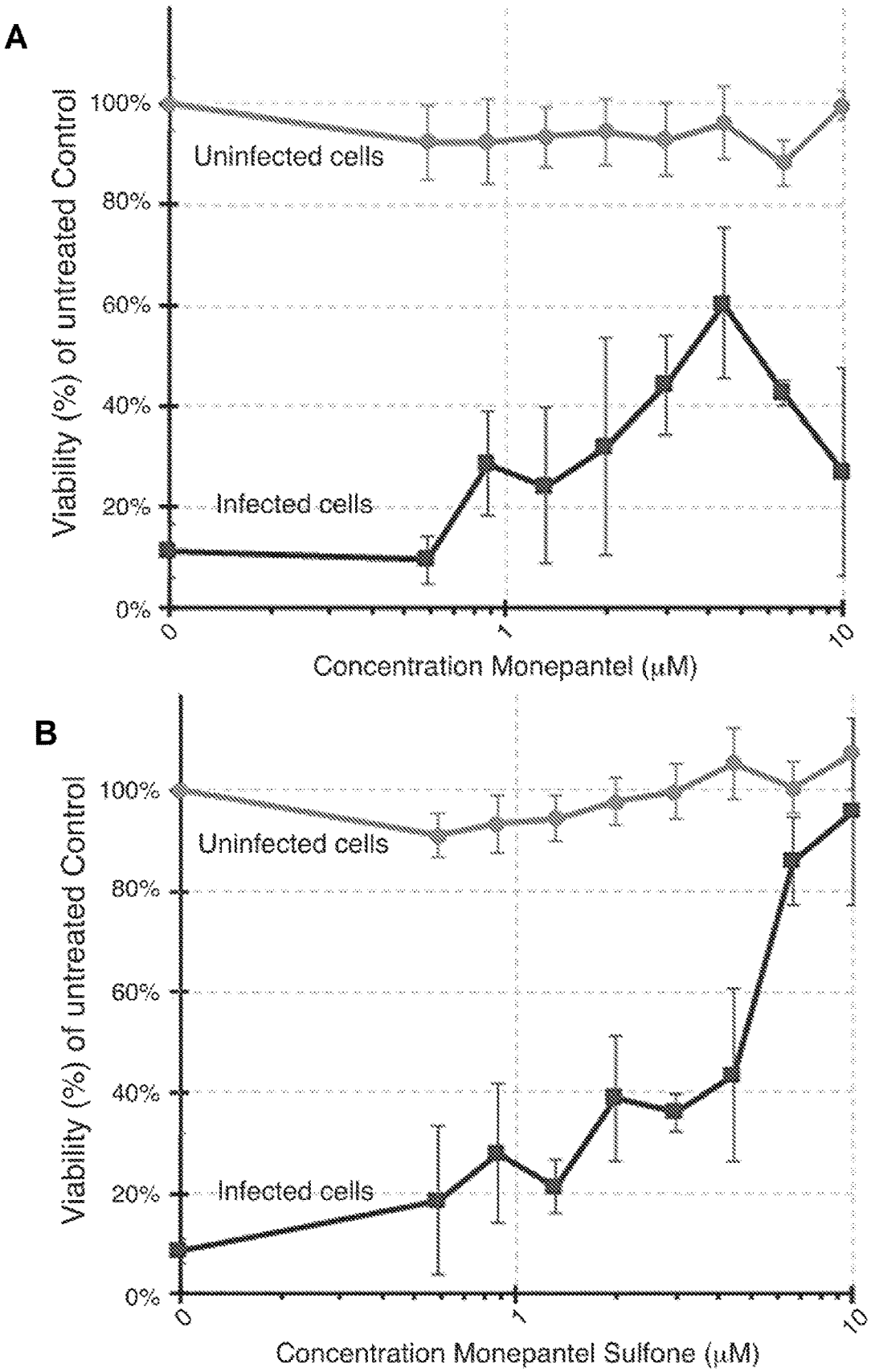
FIG. 6 shows the viability of non-human primate VERO cells infects with SARS-CoV-2 (black) and not infected with SARS-CoV-2 (grey; control) and treated with either MPL (A) or MPLS (B) at increasing concentrations in an independent laboratory. Experiments were performed three times (two repeats) with quadruplicate tests in each experiment.

In a repeat experiment testing viability of non-human primate VERO cells following infection with SARS-CoV-2, in an independent laboratory, a similar result was once again obtained (FIG. 6). A concentration of approximately 5 µM MPL protected VERO cell against cell death following infection with SARS-CoV-2. A concentration of approximately 10 µM MPLS almost completely protected VERO cell against cell death following infection with SARS-CoV-2.

Conclusions Regarding the Effect of MPL and MPLS Upon SARS-CoV-2 Infectivity of VERO Cells In Vitro MPL displays toxicity to VERO cells equivalent to other immortalised cells such as CHO and HEK cells and no significant toxicity is apparent at 8 µM or lower.

In one experiment, a concentration of 0.064 µM MPL significantly reduces SARS-CoV-2 RNA in the media and significantly reduces SARS-CoV-2 infectious virion concentration in the media. In a repeat experiment, a concentration range of 0.046 to 0.411 µM, with greatest effect at 0.137 µM MPL significantly reduces SARS-CoV-2 RNA in the media and significantly reduces SARS-CoV-2 infectious virion concentration in the media. SARS-CoV-2 RNA in VERO cell culture media and the capacity of SARS-CoV-2 containing VERO cell culture media to cause secondary toxicity following treatment of VERO cells with 8 µM MPLS in one experiment and 11 µM MPLS in another experiment are both reduced.

MPL and MPLS therefore inhibit SARS-CoV-2 infectivity of both non-human cells and human cells while appearing to have little effect upon cell toxicity. MPL and MPLS also protect cell viability in SARS-CoV-2 infected cells, evidencing the efficacy of the use of MPL for the treatment of viral infection with SARS-CoV-2.

Effect of MPL and MPLS on Human T-Lymphotropic Virus-1 (HTLV-1)

In a further example, MPL interferes with HTLV-1-directed processes essential for optimal viral propagation, and can be used as a treatment for HTLV-1-mediated disease. In one embodiment MPL impairs proliferation of HTLV-1-infected cell, induces preferential killing of HTLV-1-infected cells, and/or interferes with the expression of HTLV-1 proteins in infected cells. In a further example, MPL enhances chemotherapeutic compounds in killing HTLV-1-infected cell lines.

The effects of MPL on HTLV-1 infected cells are observable in assays of cell proliferation and death (e.g. live/Dead Multitox assay) and HTLV-1 expression e.g. HTLV-1 p 19 ELISA) in HTLV-1-transformed cell lines (MT-2 and MT-4), treated with graded concentrations of MPL alone or in combination with exemplary chemotherapeutic agents such as doxorubicin, or cyclophosphamide and compared against relative controls and a non-HTLV-1 leukaemic cell line (Jurkat).

The effects of MPL in HTLV-1 treatment are also observable in a pre-clinical model of HTLV-1 transmission and disease progression using NSG (Nod.SCID.112rgnull) mice that are reconstituted with a human immune system via engraftment of human cord blood CD34+ progenitor cells and subsequently challenged with irradiated HTLV-1-immortalised leukemic cells, which in turn transfer the virus to healthy recipient cells in vivo.

In an example, the concentrations of MPL employed for the inhibition of SARS-CoV-2 infection are also useful for the treatment of HTLV-1 infection.

The invention claimed is:

1. A method for the treatment of cancer, or one or more mTOR pathway related diseases, the method comprising administering to a patient in need thereof an amount of a compound of formula (I):

(I)

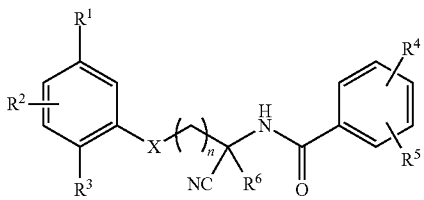

or a pharmaceutically acceptable salt or solvate thereof, sufficient to achieve a plasma concentration of said compound and/or a metabolite thereof of about 0.005 μM, about 0.01 μM, about 0.05 μM, about 0.1 μM, about 0.2 μM, about 0.3 μM, about 0.4 μM, about 0.5 μM, about 0.6 μM, about 0.7 UM, about 0.8 μM, or about 0.9 μM, wherein $R^1$, $R^2$ and $R^3$ and $R^5$ are each independently selected from H, alkyl, halogen, —$CF_3$ or —CN;

$R^4$ and $R^6$ are each independently selected from H, alkyl, halogen, alkoxy, —$CF_3$, —$OCF_3$, —$SO_2CF_3$, —$SOCF_3$ or —$SCF_3$;

X is heteroatom, N(alkyl) or NH; and n is 1 to 20;

and wherein the cancer is selected from bladder cancer, kidney cancer, liver cancer, lung cancer, esophageal cancer, gall bladder cancer, pancreatic cancer, stomach cancer, thyroid cancer, B-cell lymphoma, T-cell lymphoma, Hodgkins lymphoma, non-Hodgkins lymphoma, hairy cell lymphoma, mantle cell lymphoma, myeloma, Burkett's lymphoma, myelodysplastic syndrome, rhabdomyosarcoma, astrocytoma, neuroblastoma, schwannoma, seminoma, teratocarcinoma, osteosarcoma, or Kaposi's sarcoma, and wherein the mTOR pathway related disease is selected from Alzheimer's disease, Huntington's disease, motor neurone disease/amyotrophic lateral sclerosis, Parkinson's disease, age-related diseases, diseases related to transplant rejection, chronic inflammatory diseases, diseases related to glycogen storage, systemic lupus, diseases related to inflammation and immune activation, anaemia, leucopenia, thrombocytopenia, diseases related to stent coatings, renal insufficiency, obesity, diabetes/insulin resistance, diseases related to non-alcoholic fatty liver, polycystic kidney, fibrosis, or vial infection.

2. The method of claim 1, wherein:

$R^1$ is —CN, H or halogen;

$R^2$ is H or halogen;

$R^3$ is —$CF_3$ or halogen;

$R^4$ is —$SCF_3$, —$SOCF_3$, —$SO_2CF_3$, —$OCF_3$, or —$CF_3$;

$R^5$ is H;

$R^6$ is alkyl;

X is O; and n is 1 to 5.

3. The method of claim 2, wherein the compound of formula (I) is MPL (N-[(1R)-1-cyano-2-(5-cyano-2-trifluoromethyl-phenoxy)-1-methyl-ethyl]-4-trifluoromethylsulfanyl-benzamide):

AAD 2224 (MPL-(*R*))

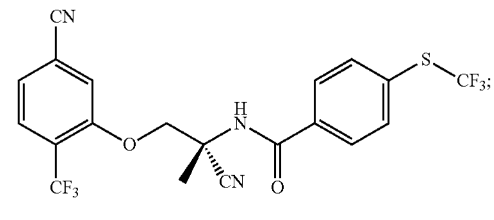

or a pharmaceutically acceptable salt or solvate thereof.

4. The method of claim 2, wherein the compound of formula (I) is MPL (N-[(1S)-1-cyano-2-(5-cyano-2-trifluoromethyl-phenoxy)-1-methyl-ethyl]-4-trifluoromethylsulfanyl-benzamide):

MPL 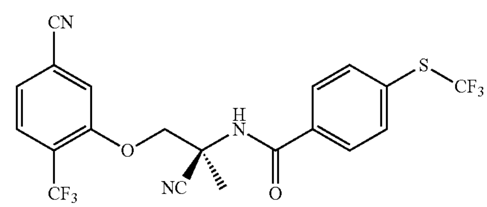 or a pharmaceutically acceptable salt or solvate thereof.

5. The method of claim 2, wherein the compound of formula (I) is monepantel sulfone (MPL-$SO_2$):

MPL-$SO_2$ 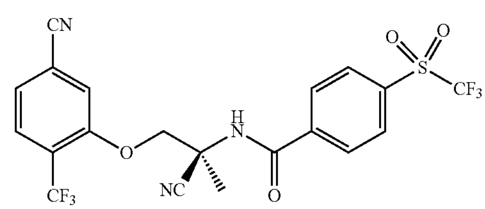 or a pharmaceutically acceptable salt or solvate thereof.

6. The method of claim 1, wherein the compound according to formula (I) is MPL, and is administered in an amount sufficient to achieve a plasma concentration of MPL-$SO_2$ of about 0.5 μM.

7. The method of claim 1, wherein the compound according to formula (I) is MPL, and is administered in an amount sufficient to achieve a plasma concentration of MPL-$SO_2$ of about 0.2 μM.

8. The method of claim 1, wherein the compound is to be administered according to a regimen of i) once daily; or ii) twice daily.

9. The method of claim 1, wherein the subject is a human.

10. The method of claim 1, wherein the subject is a non-human animal.

11. The method of claim 10, wherein the non-human animal is a canine.

12. The method of claim 1, wherein the compound is administered orally.

* * * * *